(12) United States Patent
Morero et al.

(10) Patent No.: US 10,172,632 B2
(45) Date of Patent: Jan. 8, 2019

(54) OCCLUSION BYPASSING APPARATUS WITH A RE-ENTRY NEEDLE AND A STABILIZATION TUBE

(71) Applicant: Medtronic Vascular, Inc., Santa Rosa, CA (US)

(72) Inventors: Massimo Morero, Bricherasio (IT); Claudia Vimercati, Bergamo (IT)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 106 days.

(21) Appl. No.: 14/860,913

(22) Filed: Sep. 22, 2015

(65) Prior Publication Data
US 2017/0079671 A1  Mar. 23, 2017

(51) Int. Cl.
*A61B 17/22* (2006.01)
*A61M 25/10* (2013.01)
(Continued)

(52) U.S. Cl.
CPC ......... *A61B 17/22* (2013.01); *A61M 25/0043* (2013.01); *A61M 25/0082* (2013.01);
(Continued)

(58) Field of Classification Search
CPC .......... A61B 17/22; A61B 2017/22001; A61B 2017/22051; A61B 2017/22069;
(Continued)

(56) References Cited

U.S. PATENT DOCUMENTS

| 3,568,659 A | 3/1971 | Karnegia |
| 4,552,554 A | 11/1985 | Gould et al. |

(Continued)

FOREIGN PATENT DOCUMENTS

| EP | 1765193 | 10/2012 |
| WO | WO2006105244 | 10/2006 |

(Continued)

OTHER PUBLICATIONS

U.S. Appl. No. 13/952,973, filed Jul. 29, 2013, Silvestro.
(Continued)

*Primary Examiner* — Jocelin Tanner
(74) *Attorney, Agent, or Firm* — Medler Ferro Woodhouse & Mills PLLC

(57) ABSTRACT

An occlusion bypassing apparatus for re-entering the true lumen of a vessel after subintimally bypassing an occlusion in a vessel. The apparatus includes an outer shaft component having a needle lumen there-through. A proximal end of the outer shaft component is fixed within a handle of the apparatus at a first attachment point. A stabilization tube of the apparatus is disposed within the needle lumen. A proximal end of the stabilization tube is fixed within the handle at a second attachment point that is spaced apart from the first attachment point and an elongated body and a distal end of the stabilization tube are not attached to the outer shaft component. A needle component of the apparatus is configured to be slidably disposed within the stabilization tube and removable therefrom, and the stabilization tube minimizes resistive forces exerted onto the needle component by the outer shaft component.

20 Claims, 18 Drawing Sheets

(51) Int. Cl.
*A61M 25/00* (2006.01)
*A61M 25/01* (2006.01)

(52) U.S. Cl.
CPC ...... *A61M 25/0194* (2013.01); *A61M 25/104* (2013.01); *A61B 2017/22001* (2013.01); *A61B 2017/22038* (2013.01); *A61B 2017/22065* (2013.01); *A61B 2017/22095* (2013.01); *A61M 25/0097* (2013.01); *A61M 2025/0004* (2013.01); *A61M 2025/0095* (2013.01); *A61M 2025/0197* (2013.01)

(58) Field of Classification Search
CPC ........... A61B 2017/22072; A61B 2017/22077; A61B 2017/22074; A61B 2017/22065; A61B 2017/22038; A61B 2017/22095; A61M 25/0043; A61M 25/007; A61M 25/10; A61M 25/0194; A61M 25/104; A61M 25/0082; A61M 25/0084; A61M 25/0097; A61M 2025/0079; A61M 2025/0086; A61M 2025/0085; A61M 2025/0089; A61M 2025/018; A61M 2025/1015; A61M 2025/0197; A61M 2025/0004
See application file for complete search history.

(56) References Cited

U.S. PATENT DOCUMENTS

| | | | |
|---|---|---|---|
| 4,774,949 A | 10/1988 | Fogarty | |
| 5,002,532 A | 3/1991 | Gaiser et al. | |
| 5,250,069 A * | 10/1993 | Nobuyoshi | A61M 25/1036 604/103.14 |
| 5,460,608 A | 10/1995 | Lodin et al. | |
| 5,501,667 A | 3/1996 | Verduin, Jr. | |
| 5,569,184 A | 10/1996 | Crocker et al. | |
| 5,599,324 A * | 2/1997 | McAlister | A61M 25/0026 604/523 |
| 5,667,493 A | 9/1997 | Janacek | |
| 5,707,389 A | 1/1998 | Louw et al. | |
| 5,830,222 A | 11/1998 | Makower | |
| 5,916,194 A | 6/1999 | Jacobsen et al. | |
| 5,947,994 A | 9/1999 | Louw et al. | |
| 6,068,638 A | 5/2000 | Makower | |
| 6,071,292 A | 6/2000 | Makower et al. | |
| 6,081,738 A | 6/2000 | Hinohara et al. | |
| 6,159,225 A | 12/2000 | Makower | |
| 6,178,968 B1 | 1/2001 | Louw et al. | |
| 6,190,353 B1 | 2/2001 | Makower et al. | |
| 6,196,230 B1 * | 3/2001 | Hall | A61F 2/2493 128/898 |
| 6,203,524 B1 | 3/2001 | Burney et al. | |
| 6,210,377 B1 | 4/2001 | Ouchi | |
| 6,217,527 B1 | 4/2001 | Selmon et al. | |
| 6,221,049 B1 | 4/2001 | Selmon et al. | |
| 6,231,546 B1 | 5/2001 | Milo et al. | |
| 6,231,563 B1 | 5/2001 | White et al. | |
| 6,231,587 B1 | 5/2001 | Makower et al. | |
| 6,235,000 B1 | 5/2001 | Milo et al. | |
| 6,261,260 B1 | 7/2001 | Maki et al. | |
| 6,283,983 B1 | 9/2001 | Makower et al. | |
| 6,287,317 B1 | 9/2001 | Makower et al. | |
| 6,302,875 B1 | 10/2001 | Makower et al. | |
| 6,355,027 B1 | 3/2002 | Le et al. | |
| 6,375,615 B1 | 4/2002 | Makower et al. | |
| 6,379,319 B1 | 4/2002 | Garibotto et al. | |
| 6,432,127 B1 | 8/2002 | Kim et al. | |
| 6,447,477 B2 | 9/2002 | Burney et al. | |
| 6,458,098 B1 * | 10/2002 | Kanesaka | A61B 18/1492 604/101.05 |
| 6,508,824 B1 | 1/2003 | Flaherty et al. | |
| 6,511,458 B2 | 1/2003 | Milo et al. | |
| 6,514,217 B1 | 2/2003 | Selmon et al. | |
| 6,514,228 B1 | 2/2003 | Hamilton et al. | |
| 6,544,230 B1 * | 4/2003 | Flaherty | A61B 17/22 604/164.09 |
| 6,579,311 B1 | 6/2003 | Makower | |
| 6,602,241 B2 | 8/2003 | Makower et al. | |
| 6,655,386 B1 | 12/2003 | Makower et al. | |
| 6,669,709 B1 | 12/2003 | Cohn et al. | |
| 6,709,444 B1 | 3/2004 | Makower | |
| 6,719,725 B2 | 4/2004 | Milo et al. | |
| 6,726,677 B1 | 4/2004 | Makower et al. | |
| 6,746,464 B1 | 6/2004 | Makower et al. | |
| 7,004,173 B2 | 2/2006 | Sparks et al. | |
| 7,059,330 B1 | 6/2006 | Makower et al. | |
| 7,066,914 B2 | 6/2006 | Andersen | |
| 7,141,041 B2 | 11/2006 | Seward | |
| 7,179,270 B2 | 2/2007 | Makower et al. | |
| 7,316,655 B2 | 1/2008 | Garibotto et al. | |
| 7,357,794 B2 | 4/2008 | Makower et al. | |
| 7,534,223 B2 | 5/2009 | Boutilette et al. | |
| 7,606,615 B2 | 10/2009 | Makower et al. | |
| 7,637,870 B2 | 12/2009 | Flaherty et al. | |
| 7,729,738 B2 | 6/2010 | Flaherty et al. | |
| 7,762,985 B2 | 7/2010 | Kabrick et al. | |
| 7,833,197 B2 | 11/2010 | Boutilette et al. | |
| 7,854,727 B2 | 12/2010 | Belsley | |
| RE42,049 E | 1/2011 | Schroeder et al. | |
| 7,878,986 B2 | 2/2011 | Jen et al. | |
| 7,938,819 B2 | 5/2011 | Kugler et al. | |
| 8,083,727 B2 | 12/2011 | Kugler et al. | |
| 8,172,863 B2 | 5/2012 | Robinson et al. | |
| 8,202,246 B2 | 6/2012 | Kugler et al. | |
| 8,221,357 B2 | 7/2012 | Boutilette | |
| 8,226,566 B2 | 7/2012 | Nita | |
| 8,241,311 B2 | 8/2012 | Ward et al. | |
| 8,257,382 B2 | 9/2012 | Rottenberg et al. | |
| 8,323,261 B2 | 12/2012 | Kugler et al. | |
| 8,337,425 B2 | 12/2012 | Olson et al. | |
| 8,388,876 B2 | 3/2013 | Boutilette et al. | |
| 8,460,254 B2 | 6/2013 | Belsley | |
| 8,486,022 B2 | 7/2013 | Ludwig et al. | |
| 8,496,679 B2 | 7/2013 | Robinson et al. | |
| 8,512,310 B2 | 8/2013 | Kugler et al. | |
| 8,535,245 B2 | 9/2013 | Jen et al. | |
| 8,556,857 B2 | 10/2013 | Boutilette | |
| 9,060,802 B2 | 6/2015 | Kugler | |
| 9,095,374 B2 | 8/2015 | Piccagli | |
| 2001/0000041 A1 | 3/2001 | Selmon et al. | |
| 2002/0072706 A1 | 6/2002 | Hiblar et al. | |
| 2003/0163154 A1 | 8/2003 | Miyata et al. | |
| 2004/0073165 A1 | 4/2004 | Musbach et al. | |
| 2004/0167554 A1 | 8/2004 | Simpson et al. | |
| 2004/0186506 A1 | 9/2004 | Simpson et al. | |
| 2005/0021003 A1 | 1/2005 | Caso et al. | |
| 2005/0149062 A1 | 7/2005 | Carroll | |
| 2005/0159728 A1 | 7/2005 | Armour et al. | |
| 2005/0171478 A1 | 8/2005 | Selmon et al. | |
| 2005/0267459 A1 | 12/2005 | Belhe et al. | |
| 2006/0074442 A1 | 4/2006 | Noriega et al. | |
| 2006/0094930 A1 | 5/2006 | Sparks et al. | |
| 2006/0241564 A1 | 10/2006 | Corcoran et al. | |
| 2006/0276749 A1 | 12/2006 | Selmon et al. | |
| 2007/0123925 A1 | 5/2007 | Benjamin et al. | |
| 2008/0125748 A1 | 5/2008 | Patel | |
| 2008/0140101 A1 | 6/2008 | Carley et al. | |
| 2008/0147000 A1 | 6/2008 | Seibel et al. | |
| 2008/0249464 A1 | 10/2008 | Spencer et al. | |
| 2009/0124899 A1 | 5/2009 | Jacobs et al. | |
| 2009/0192584 A1 * | 7/2009 | Gerdts | A61F 2/95 623/1.11 |
| 2009/0209910 A1 | 8/2009 | Kugler et al. | |
| 2010/0010522 A1 | 1/2010 | Shturman | |
| 2010/0063534 A1 | 3/2010 | Kugler et al. | |
| 2011/0144677 A1 | 6/2011 | Ward et al. | |
| 2011/0264125 A1 | 10/2011 | Wilson et al. | |
| 2011/0276079 A1 | 11/2011 | Kugler et al. | |
| 2012/0053485 A1 | 3/2012 | Bloom | |
| 2012/0095485 A1 | 4/2012 | Cully et al. | |
| 2012/0283571 A1 | 11/2012 | Nita | |
| 2012/0283761 A1 | 11/2012 | Rosenthal et al. | |

(56) References Cited

U.S. PATENT DOCUMENTS

| | | | |
|---|---|---|---|
| 2012/0323220 A1* | 12/2012 | Mackay, II | A61B 18/12 604/510 |
| 2012/0323251 A1 | 12/2012 | Kugler et al. | |
| 2012/0323269 A1 | 12/2012 | Rottenberg et al. | |
| 2013/0006167 A1 | 1/2013 | Alvarez | |
| 2013/0006173 A1 | 1/2013 | Alvarez et al. | |
| 2013/0006282 A1 | 1/2013 | Wilkinson | |
| 2013/0072957 A1 | 3/2013 | Anderson | |
| 2013/0103070 A1 | 4/2013 | Kugler et al. | |
| 2013/0116622 A1 | 5/2013 | Takagi | |
| 2013/0150880 A1 | 6/2013 | Anderson | |
| 2013/0158519 A1 | 6/2013 | Boutilette et al. | |
| 2013/0245430 A1 | 9/2013 | Selmon et al. | |
| 2013/0261545 A1 | 10/2013 | Osypka | |
| 2013/0296907 A1 | 11/2013 | Robinson et al. | |
| 2013/0304108 A1 | 11/2013 | Weber et al. | |
| 2013/0310868 A1 | 11/2013 | Kugler et al. | |
| 2013/0317528 A1 | 11/2013 | Anderson et al. | |
| 2014/0018732 A1 | 1/2014 | Bagaoisan et al. | |
| 2014/0142607 A1* | 5/2014 | Cage | A61M 25/0054 606/185 |
| 2014/0214057 A1 | 7/2014 | Piccagli | |
| 2014/0277053 A1 | 9/2014 | Wang et al. | |
| 2015/0174371 A1* | 6/2015 | Schaeffer | A61M 25/0194 606/185 |

FOREIGN PATENT DOCUMENTS

| | | |
|---|---|---|
| WO | WO2008120209 | 10/2008 |
| WO | WO2009144561 | 12/2009 |
| WO | WO2013003757 | 1/2013 |
| WO | WO2013164825 | 11/2013 |
| WO | WO2014039096 | 3/2014 |

OTHER PUBLICATIONS

U.S. Appl. No. 13/952,981, filed Jul. 29, 2013, Silvestro.
U.S. Appl. No. 14/197,803, filed Mar. 5, 2014, Silvestro.
U.S. Appl. No. 14/058,444, filed Oct. 21, 2013, Silvestro.
Shin et al. "Limitations of the Outback LTD re-entry device in femoropopliteal chronic total occlusions." Journal of Vascular Surgery, vol. 53, 5; 2010.
A. Bolia "Subintimial Angioplasty, the Way Forward" Acta chir belg, 2004, 104, 547-554.
Karkos et al. "Subintimal Recanalization of the Femoropopliteal Segment to Promote Healing of an Ulcerated Below-Knee Amputation Stump" J Endovasc Ther 2006;13:420-423.
Glasby et al. "Subintimal Angioplasty" Review, pp. 12-16, 2008.
Bolia A. "Subintimal Angioplasty, Tips and Technique: How Long Can You Go?".
International Search Report dated Jan. 5, 2017 in corresponding International Patent Application No. PCT/US2016/051827.
Written Opinion dated Jan. 5, 2017 in corresponding International Patent Application No. PCT/US2016/051827.

\* cited by examiner

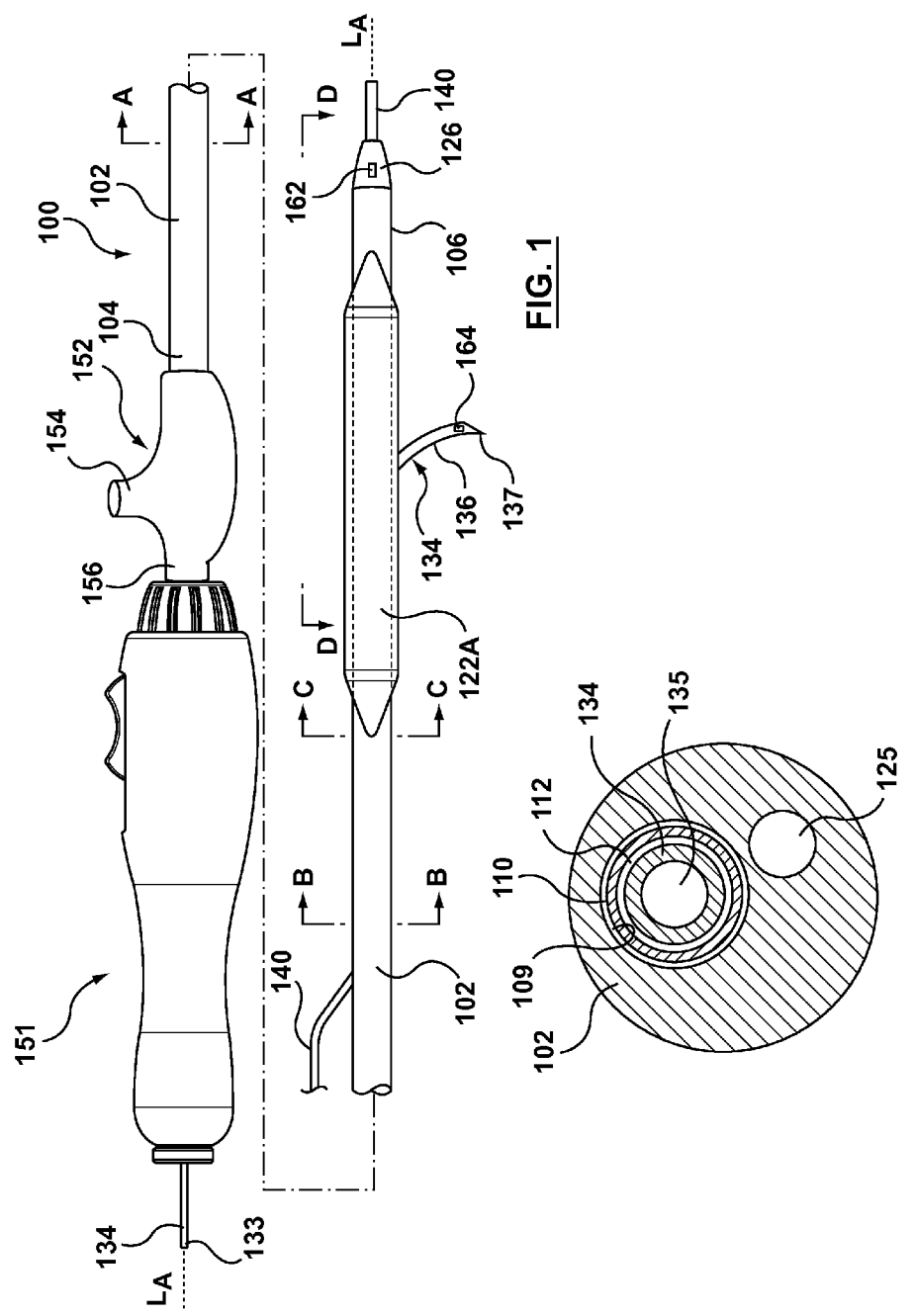

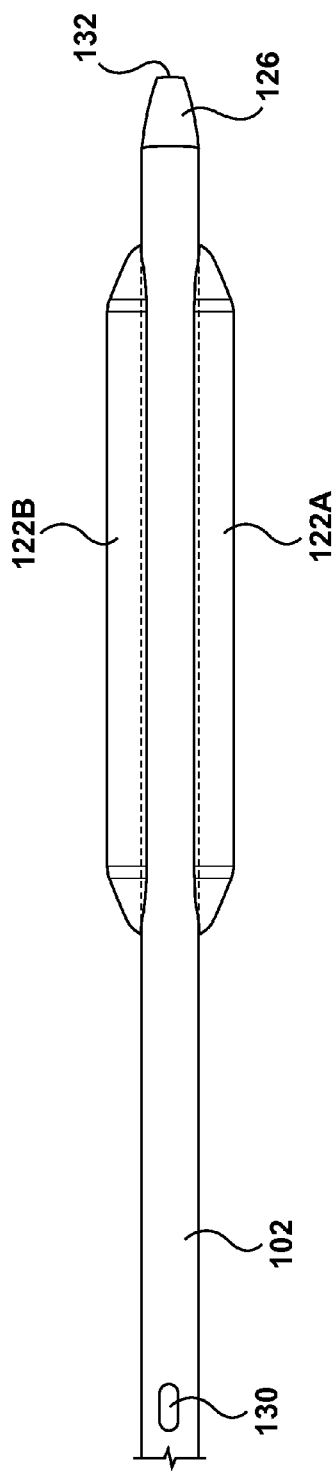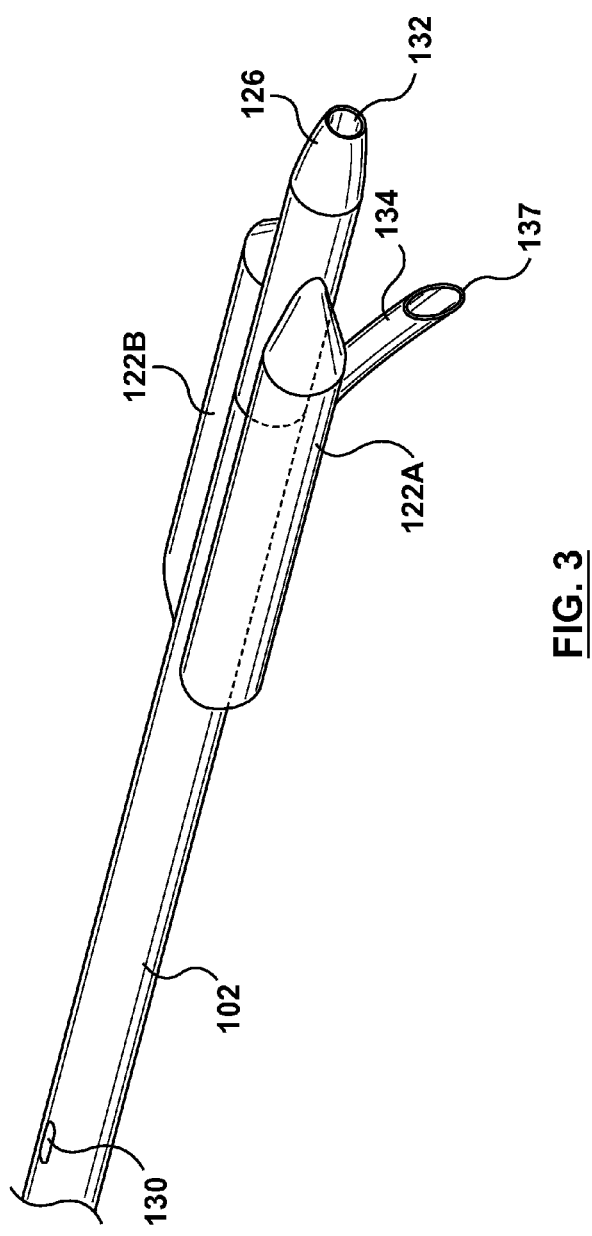

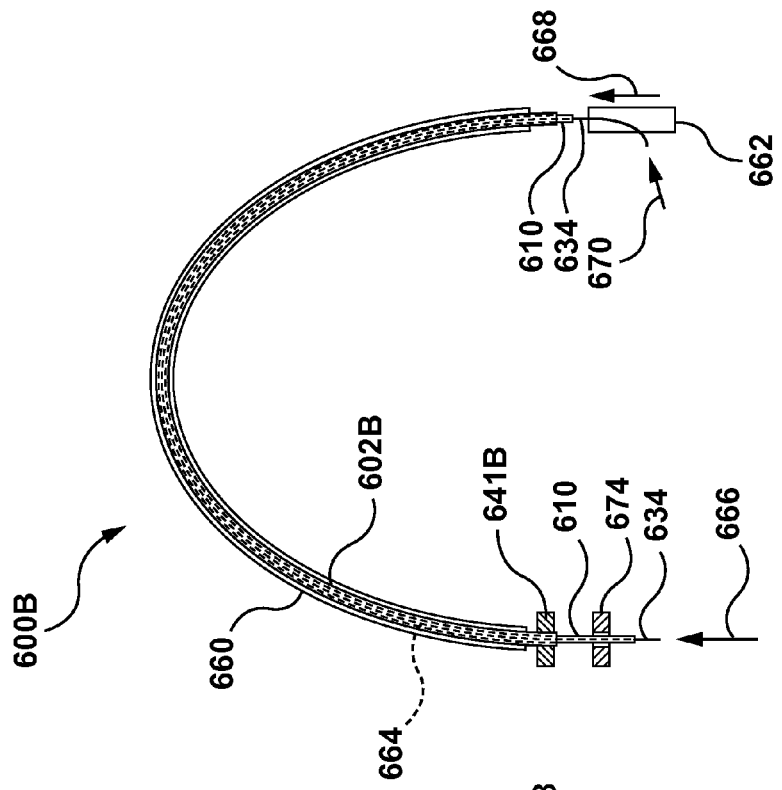
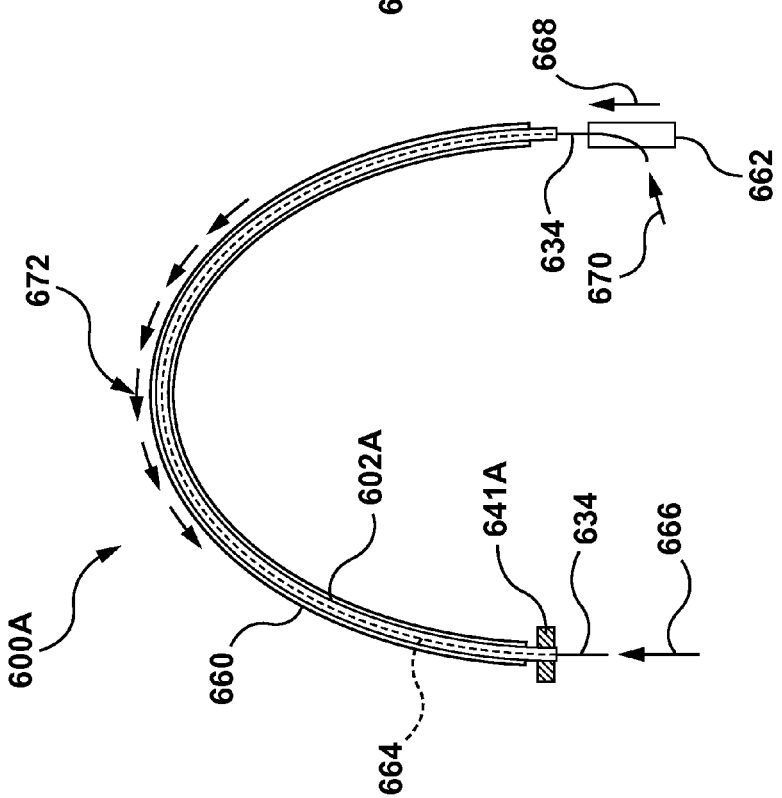

— OCCLUSION BYPASSING APPARATUS WITH A RE-ENTRY NEEDLE AND A STABILIZATION TUBE

FIELD OF THE INVENTION

The invention relates generally to an occlusion bypassing apparatus and methods of using the apparatus for subintimally bypassing a blockage in a blood vessel such as a chronic total occlusion and reentering the true lumen of the blood vessel beyond the blockage.

BACKGROUND OF THE INVENTION

Cardiovascular disease, including atherosclerosis, is a serious ailment for many people that may in some cases lead to death. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel.

The anatomy of arteries varies widely from patient to patient. Often a patient's arteries are irregularly shaped, highly tortuous and very narrow. The tortuous configuration of the arteries may present difficulties to a clinician in advancement of the balloon catheter to a treatment site. In addition, in some instances, the extent to which the lumen is narrowed at the treatment site is so severe that the lumen is completely or nearly completely obstructed, which may be described as a total occlusion. Total or near-total occlusions in arteries can prevent all or nearly all of the blood flow through the affected arteries. If the occlusion has been established for a long period of time, the lesion may be referred to as a chronic total occlusion or CTO. Chronic total occlusions can occur in coronary as well as peripheral arteries. Chronic total occlusions are often characterized by extensive plaque formation and typically include a fibrous cap surrounding softer plaque material. This fibrous cap may present a surface that is difficult to penetrate with a conventional medical guidewire.

A number of devices have been developed and/or used for the percutaneous interventional treatment of CTOs, such as stiffer guidewires, low-profile balloons, laser light emitting wires, atherectomy devices, drills, drug eluting stents, and re-entry catheters. The factor that is most determinative of whether the physician can successfully recannalize a CTO is the physician's ability to advance a suitable guidewire from a position within the true lumen of the artery proximal to the CTO lesion, across the CTO lesion, i.e., either through the lesion or around it, and then back into the true lumen of the artery at a location distal to the CTO lesion.

In some cases, such as where the artery is totally occluded by hard, calcified atherosclerotic plaque, the guidewire may tend to deviate to one side and penetrate through the intima of the artery, thereby creating a neo-lumen called a "subintimal tract" i.e., a penetration tract formed within the wall of the artery between the intima and adventitia. In these cases, the distal end of the guidewire may be advanced to a position distal to the lesion but remains trapped within the subintimal tract. In such instances, it is then necessary to divert or steer the guidewire from the subintimal tract back into the true lumen of the artery at a location distal to the CTO lesion. The process of manipulating the guidewire to reenter the artery lumen is often difficult and solutions have been proposed utilizing various means for dealing with such a problem.

A number of catheter-based devices have been heretofore useable to redirect subintimally trapped guidewires back into the true lumen of the artery. Included among these are a variety of catheters having laterally deployable cannulae, i.e., hollow needles. For example, some catheter systems utilize a penetrator or needle that, thanks to the presence of an on-board imaging system (IVUS), exits through a side exit port of the catheter to puncture the intimal layer distal of the CTO to re-enter the true lumen of the vessel. A second guidewire is then passed through the laterally deployed needle and is advanced into the true lumen of the artery. However, a need in the art still exists for other medical catheters or systems that consistently and reliably direct subintimally advanced guidewires back into the true lumen of the artery for the treatment of a CTO.

BRIEF SUMMARY OF THE INVENTION

Embodiments hereof are directed to an apparatus for bypassing an occlusion in a blood vessel. The apparatus includes a handle, an outer shaft component, a stabilization tube, and a needle component. The outer shaft component has a side port proximal to a distal end thereof and has a needle lumen there-through that includes a curved distal portion that bends from a longitudinal axis of the apparatus and terminates at the side port of the outer shaft component. A proximal end of the outer shaft component is fixed within the handle at a first attachment point. The stabilization tube has an elongated body extending between a proximal end and a distal end thereof, and the elongated body is disposed within the needle lumen of the outer shaft component. The proximal end of the stabilization tube is fixed within the handle at a second attachment point that is spaced apart from the first attachment point and the elongated body and distal end of the stabilization tube are not attached to the outer shaft component. The needle component is configured to be slidably disposed within the stabilization tube and removable therefrom, and the stabilization tube minimizes resistive forces exerted onto the needle component by the outer shaft component.

In another embodiment hereof, the apparatus includes a handle, an outer shaft component, at least one balloon, a stabilization tube, and a needle component. The outer shaft component has a side port proximal to a distal end thereof and a distal port at the distal end thereof. The outer shaft component includes a needle lumen there-through that includes a curved distal portion that bends from a longitudinal axis of the apparatus and terminates at the side port of the outer shaft component, an inflation lumen there-through for receiving an inflation fluid, and a guidewire lumen that extends along at least a portion of the outer shaft component and terminates at the distal port at the distal end of the outer shaft component. A proximal end of the outer shaft component is fixed within the handle at a first attachment point. The at least one balloon is disposed on the outer shaft component proximal to the distal end thereof, and the balloon is in fluid communication with the inflation lumen of the outer shaft component. The stabilization tube has an elongated body extending between a proximal end and a distal end thereof, and the elongated body is disposed within the needle lumen of the outer shaft component. The proximal end of the stabilization tube is fixed within the handle at a second attachment point that is spaced apart from the first attachment point and the elongated body and distal end of the stabilization tube are not attached to the outer shaft component. The needle component is configured to be slidably disposed within the stabilization tube and removable therefrom, and the stabilization tube minimizes resistive forces exerted onto the needle component by the outer shaft component.

In another embodiment hereof, the apparatus for bypassing an occlusion in a blood vessel includes a handle, an outer shaft component, a stabilization tube, a needle housing, and a needle component. The outer shaft component has a side port proximal to a distal end thereof and includes a needle lumen there-through that includes a curved distal portion that bends from a longitudinal axis of the apparatus and terminates at the side port of the outer shaft component. A proximal end of the outer shaft component is fixed within the handle at a first attachment point. The stabilization tube has an elongated body extending between a proximal end and a distal end thereof, and the elongated body is disposed within the needle lumen of the outer shaft component. The proximal end of the stabilization tube is fixed within the handle at a second attachment point that is spaced apart from the first attachment point and the elongated body and distal end of the stabilization tube are not attached to the outer shaft component. The needle housing is disposed within the needle lumen of the outer shaft component. The needle housing includes a curved distal portion that defines the curved distal portion of the needle lumen and a transition proximal portion that has a variable flexibility along its length that decreases in a distal direction. The distal end of the stabilization tube is proximal to a proximal end of the needle housing. The needle component is configured to be slidably disposed within the stabilization tube and removable therefrom. The needle component has a curved distal end with the same curvature as the curved distal portion of the needle lumen of the outer shaft component and a distal tip configured to penetrate a wall of the vessel. In a first configuration of the apparatus, the curved distal end of the needle component is held in a straightened form within the needle housing. In a second configuration of the apparatus, the curved distal end of the needle component extends from the side port of the outer shaft component and bends from the longitudinal axis of the apparatus.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of an occlusion bypassing apparatus according to an embodiment hereof, wherein the occlusion bypassing apparatus is shown advanced over a guidewire in a deployed configuration in which a needle component thereof is extended through a side port of an outer shaft component and lateral balloons of the occlusion bypassing apparatus are expanded.

FIG. 1A is a cross-sectional view of the occlusion bypassing apparatus of FIG. 1 taken along line A-A thereof, wherein line A-A is located proximal to a proximal guidewire port of the occlusion bypassing apparatus.

FIG. 2 is a top view of a distal portion of the occlusion bypassing apparatus of FIG. 1 with the guidewire removed.

FIG. 3 is a perspective view of a distal portion of the occlusion bypassing apparatus of FIG. 1 with the guidewire removed.

FIG. 6A is a schematic illustration of the function of a stabilization tube of an occlusion bypassing apparatus or catheter, wherein the catheter is depicted within a curved vessel and the catheter does not include a stabilization tube.

FIG. 6B is a schematic illustration of the function of a stabilization tube of an occlusion bypassing apparatus or catheter, wherein the catheter is depicted within a curved vessel and the catheter includes a stabilization tube.

DETAILED DESCRIPTION OF THE INVENTION

Figure 1C:
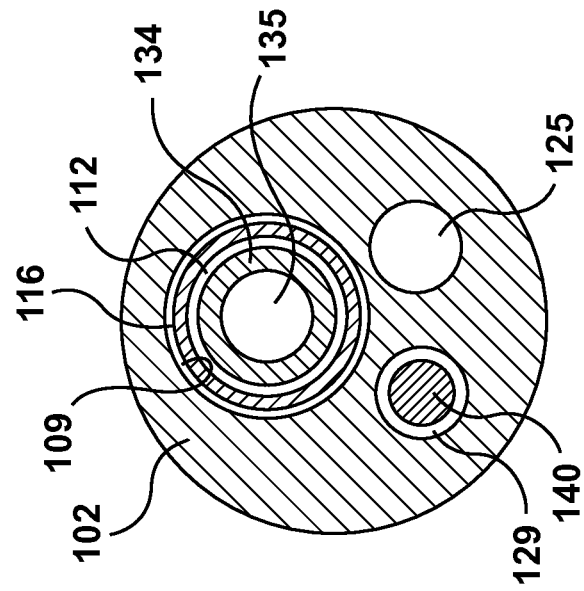
FIG. 1C is a cross-sectional view of the occlusion bypassing apparatus of FIG. 1 taken along line C-C thereof, wherein line C-C is located distal to a proximal guidewire port of the occlusion bypassing apparatus and along a needle housing of an stabilization tube of the occlusion bypassing apparatus.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as smaller diameter peripheral or coronary arteries, the invention may also be used in any other body passageways where it is deemed useful. Although the description of the invention generally refers to an apparatus and method of bypassing a vessel blockage in a proximal-to-distal direction, i.e. antegrade or with the blood flow, the invention may be used equally well to bypass a vessel blockage in a distal-to-proximal direction, i.e. retrograde or against the blood flow, if access is available from that direction. In other terms, the apparatus and method described herein may be considered to bypass a vessel blockage from a near side of the blockage to a far side of the blockage. Furthermore, there is no intention to be bound by any expressed or implied theory presented in the preceding technical field, background, brief summary or the following detailed description.

Embodiments hereof relate to an apparatus and method for re-entering the true lumen of a vessel after subintimally bypassing an occlusion in a blood vessel such as a chronic total occlusion (CTO) of an artery. The apparatus includes a handle, an outer shaft component, a stabilization tube which is disposed within the outer shaft component, and a needle component which is configured to be slidably disposed within the stabilization tube and removable therefrom. The stabilization tube minimizes or eliminates resistive forces exerted onto the needle component by the outer shaft component. More particularly, the outer shaft component and the stabilization tube are fixed within the handle at spaced apart attachment or fixation points so that the stabilization tube essentially hides the resistance exerted by the advancement of the needle component to the outer shaft component. Without the stabilization tube, friction or resistive force exists between the needle component and the outer shaft component while the needle component is deployed, and such resistive force tends to elongate the outer shaft component and jeopardizes the overall performance of the apparatus. However, with the stabilization tube, such resistive force remains almost completely within the stabilization tube, thus preventing the outer shaft component from being exposed to such force or stress and thus preserving the overall performance of the apparatus.

Figure 1B:
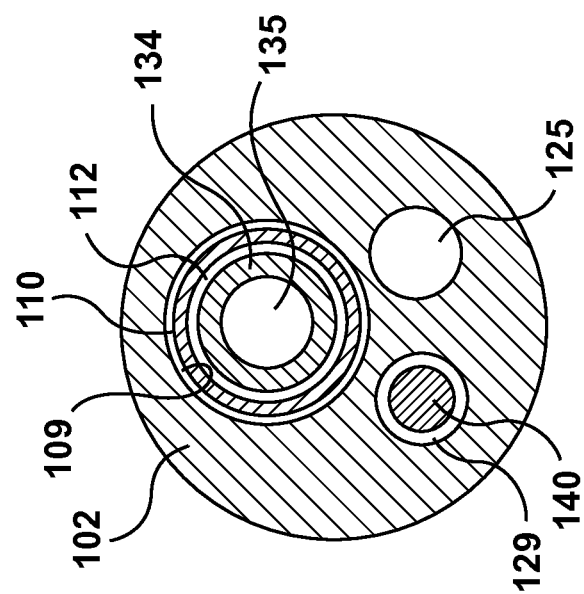
FIG. 1B is a cross-sectional view of the occlusion bypassing apparatus of FIG. 1 taken along line B-B thereof, wherein line B-B is located distal to a proximal guidewire port of the occlusion bypassing apparatus and along a body portion of an stabilization tube of the occlusion bypassing apparatus.

More particularly, with reference to the figures, FIG. 1 illustrates a side view of an occlusion bypassing apparatus 100 in its deployed configuration, with FIG. 1A, FIG. 1B, FIG. 1C being cross-sectional views which are taken at different longitudinal locations along occlusion bypassing apparatus 100 as described in more detail herein. FIG. 2 and FIG. 3 are top and perspective views, respectively, of a distal portion of occlusion bypassing apparatus 100. Occlusion bypassing apparatus 100 includes an outer shaft component 102 with first and second lateral balloons 122A, 122B for stabilization or anchoring thereof. Outer shaft component 102 is a tubular or cylindrical element that defines a plurality of lumens formed by multi-lumen profile extrusion. More particularly, outer shaft component 102 includes a needle lumen 109 for housing a stabilization tube 110 and a needle housing 116, a guidewire lumen 129 for housing a guidewire 140, and an inflation lumen 125 for receiving an inflation fluid. As will be explained in more detail herein, outer shaft component 102 has a side port 108 (see FIGS. 8 and 9) proximal to a distal end 106 thereof and a distal guidewire port 132 at distal end 106. Needle lumen 109 includes a curved distal portion that bends from a longitudinal axis of occlusion bypassing apparatus 100 and terminates at side port 108 of outer shaft component 102. Stabilization tube 110 is disposed within or through a portion of needle lumen 109 of outer shaft component 102, and a needle component 134 is slidably and removably disposed within a lumen 112 of stabilization tube 110. As used herein, "slidably" denotes back and forth movement in a longitudinal direction. As will be explained in more detail herein, stabilization tube 110 minimizes or eliminates resistive forces exerted onto needle component 134 by outer shaft component 102. While occlusion bypass apparatus 100 is stabilized or anchored within a subintimal space of a vessel, a curved distal end 136 of needle component 134 is advanced out of side port 108 of outer shaft component 102 towards the true lumen of the vessel. In FIGS. 1-3, curved distal end 136 of needle component 134 is shown extended from side port 108 of outer shaft component 102 in a deployed configuration that is suitable for puncturing the vessel wall to gain access to the true lumen.

Outer shaft component 102 includes a first lateral balloon 122A and a second lateral balloon 122B mounted on a distal portion thereof. A flexible distal tip 126 is coupled to distal end 106 of outer shaft component 102. As best shown on the top view of FIG. 2 and the perspective view of FIG. 3, lateral balloons 122A, 122B are disposed in parallel on opposing sides of outer shaft component 102. Side port 108 of outer shaft component 102, through which needle component 134 is advanced, is proximal to distal end 106 thereof. In an embodiment, side port 108 is disposed midway along the length of lateral balloons 122A, 122B in order to optimize the stabilization function of the balloons. Although shown with dual lateral balloons, embodiments hereof may utilize other balloon configurations for stabilization of the occlusion bypassing apparatus, including but not limited to a single cylindrical balloon that circumferentially surrounds the outer shaft component. If a single cylindrical balloon is utilized, the side port of the outer shaft component may be moved slightly proximal of the balloon so that the balloon does not surround the side port. A proximal end 104 of outer shaft component 102 extends out of the patient and is coupled to a hub 152 of a handle 151. Inflation lumen 125 of outer shaft component 102 is in fluid communication with first lateral balloon 122A and second lateral balloon 122B to allow inflation fluid received through hub 152 to be concurrently delivered to both of the lateral balloons. As would be understood by one of ordinary skill in the art of balloon catheter design, hub 152 includes a hemostatic valve 156 to accommodate insertion of occlusion bypassing apparatus 100 and a luer 154 or other type of fitting that may be connected to a source of inflation fluid (not shown) and may be of another construction or configuration without departing from the scope of the present invention. When inflated, lateral balloons 122A, 122B anchor outer shaft component 102 within the anatomy, more particularly within the subintimal space of the vessel wall when utilized in the treatment of a CTO, so as to provide stability to occlusion bypassing apparatus 100.

Guidewire lumen 129 is relatively short and extends only through a distal portion of outer shaft component 102 for accommodating guidewire 140 in a so-called rapid-exchange configuration. More particularly, guidewire lumen 129 extends from a proximal guidewire port 130 (see FIGS. 2 and 3) to distal guidewire port 132 (see FIGS. 2 and 3). Guidewire 140 is omitted from FIG. 2 and FIG. 3 in order to clearly show proximal and distal guidewire ports 130, 132, respectively. With reference to the cross-sectional views of FIG. 1A, FIG. 1B, FIG. 1C, which are taken at different longitudinal locations along occlusion bypassing apparatus 100, guidewire lumen 129 extends within outer shaft component 102 in longitudinal locations distal to proximal guidewire port 130, i.e., as shown in FIG. 1B and FIG. 1C, but does not extend within outer shaft component proximal to proximal guidewire port 130, i.e., as shown in FIG. 1A. Guidewire lumen 129 may have a length between 5 cm and 20 cm. In an embodiment, outer shaft component 102 may be sized to be used with a 5F introducer sheath with guidewire lumen 129 being sized to accommodate a guidewire having an outer diameter of 0.014 inch.

Outer shaft component 102 may be formed of one or more polymeric materials, non-exhaustive examples of which include polyethylene, polyethylene block amide copolymer (PEBA), polyamide and/or combinations thereof, either laminated, blended or co-extruded. Optionally, outer shaft component 102 or some portion thereof may be formed as a composite having a reinforcement layer incorporated within a polymeric body in order to enhance strength and/or flexibility and/or torqueability. Suitable reinforcement layers include braiding, wire mesh layers, embedded axial wires, embedded helical or circumferential wires, hypotubes, and the like. In one embodiment, for example, at least a proximal portion of outer shaft component 102 may be formed from a reinforced polymeric tube.

Other types of construction are suitable for outer shaft component 102. In another embodiment (not shown), rather than a single inflation lumen that concurrently delivers inflation fluid to both first and second lateral balloons 122A, 122B as described herein, the outer shaft component may include two inflation lumens that separately deliver inflation fluid to the first and second lateral balloons. Further, although embodiments above are described with a relatively short guidewire lumen in a rapid-exchange configuration, embodiments hereof may be modified to have an over-the-wire configuration in which the guidewire lumen extends the entire length of the outer shaft component. For example, in order to provide an over-the-wire configuration, the relatively short guidewire lumen of the above embodiment may be modified to extend the entire length of the outer shaft component.

Figure 4:
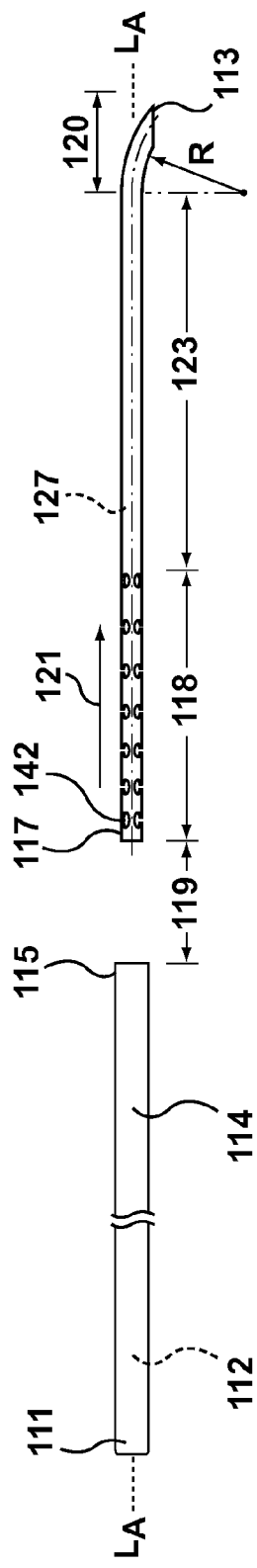
FIG. 4 is a side view of the stabilization tube and a needle housing of the occlusion bypassing apparatus of FIG. 1, wherein the stabilization tube and needle housing are removed from the occlusion bypassing apparatus for illustrative purposes only.

As stated above, needle lumen 109 of outer shaft component 102 houses stabilization tube 110 and needle housing 116. More particularly, stabilization tube 110 and needle housing 116 are separate or distinct components that lay within needle lumen 109 of outer shaft component 102. Stabilization tube 110 and needle housing 116 are disposed within longitudinally spaced-apart locations of needle lumen 109 of outer shaft component 102. Stabilization tube 110 is positioned proximal to needle housing 116, which is disposed at a distal portion of needle lumen 109 of outer shaft component 102. Accordingly, with reference back to FIG. 1, FIG. 1B is a cross-sectional view taken along line B-B of FIG. 1 that shows needle component 134 within stabilization tube 110, while FIG. 1C is a cross-sectional view taken along line C-C of FIG. 1 (which is taken at a more distal longitudinal location along occlusion bypassing apparatus 100) that shows needle component 134 within needle housing 116. As best shown in FIG. 4, which is a side view of stabilization tube 110 and needle housing 116 removed from occlusion bypassing apparatus 100 for illustrative purposes only, a distal end 115 of stabilization tube 110 is proximal to a proximal end 117 of needle housing 116. Notably, distal end 115 of stabilization tube 110 is longitudinally spaced apart from proximal end 117 of needle housing 116 by a gap 119 so that stabilization tube 110 and needle housing 116 do not overlap, abut, or otherwise contact each other. In an embodiment hereof, gap 119 may range between 1.0 and 1.5 inches. The particular dimension for gap 119 depends upon various factors including the material selected for stabilization tube 110 as well as the tortuosity of the vasculature path within which apparatus 100 is intended to be deployed.

Stabilization tube 110 is a tubular or cylindrical shaft component that includes an elongated body portion 114 that extends substantially parallel with a longitudinal axis $L_A$ of occlusion bypassing apparatus 100. Stabilization tube 110 defines a lumen 112 that extends from a proximal end 111 to distal end 115 thereof, with lumen 112 being sized and configured to slidably and removably receive needle component 134 there-through. As will be described in more detail herein, needle housing 116 is a tubular or cylindrical shaft component that includes a proximal transition portion 118 with a variable flexibility and a curved distal portion 120. Needle housing 116 is disposed at the distal portion of needle lumen 109, with proximal end 117 being embedded into or expanded into apposition with the polymeric material of outer shaft component 102. Curved distal portion 120 of needle housing 116 bends from longitudinal axis $L_A$ of occlusion bypassing apparatus 100 and terminates at side port 108 of outer shaft component 102. Needle housing 116 defines a lumen 127 that extends from proximal end 117 to a distal end 113 thereof, with lumen 127 also being sized and configured to slidably and removably receive needle component 134 there-through. When needle component 134 is positioned within occlusion bypassing apparatus 100, needle component 134 is disposed or extends through lumen 112 of stabilization tube 110, through lumen 109 of outer shaft component 102 along gap 119 between stabilization tube 110 and needle housing 116, and through lumen 127 of needle housing 116.

In an embodiment hereof, stabilization tube 110 is an elongate polymeric tube while needle housing 116 is a metallic tube of a relatively shorter length than the length of stabilization tube 110 with needle housing 116 being less flexible or stiffer than stabilization tube 110. Typically, the needle housing length is about 2-5% of the stabilization tube length. Thus, stabilization tube 110 surrounds needle component 134 for the majority of its length and prevents contact between needle component 134 and outer shaft component 102. For example, stabilization tube 110 may be a polymeric tube formed of a flexible polymeric material, non-exhaustive examples of which include polyethylene, polyethylene block amide copolymer (PEBA), polyamide and/or combinations thereof. Polymeric material ensures that stabilization tube 110, and thus occlusion bypassing apparatus 100, has the required flexibility necessary for in situ delivery. Needle housing 116 is preferably formed from a shape memory material such as nitinol to ensure high flexibility of occlusion bypassing apparatus 100 during advancement through the vasculature. Alternatively, needle housing 116 may be formed from a metallic resilient material such as steel or spring temper stainless steel.

Figure 5:
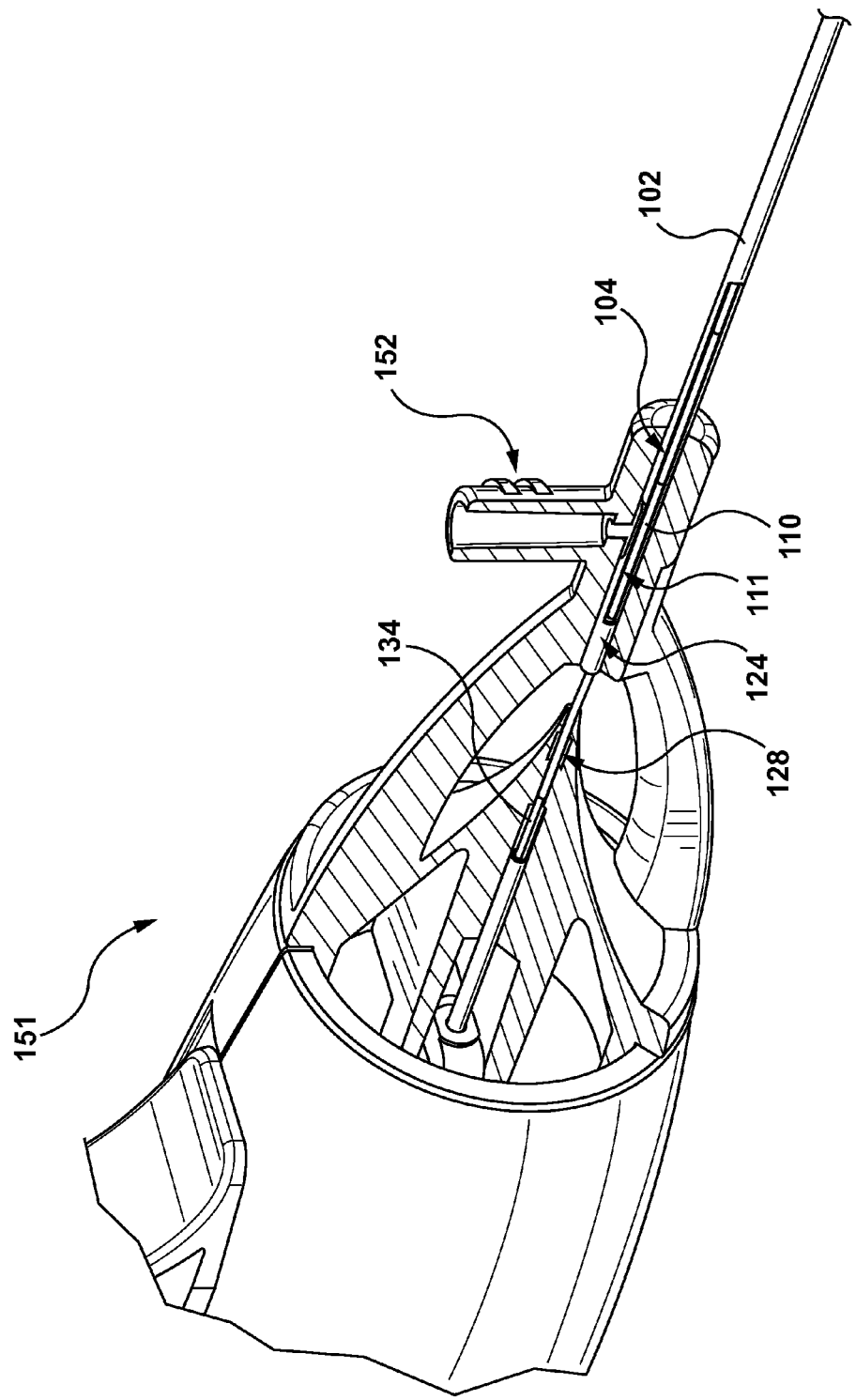
FIG. 5 is a perspective sectional view of a handle of the occlusion bypassing apparatus of FIG. 1.

As best shown on FIG. 5, proximal end 104 of outer shaft component 102 is fixed within handle 151 at a first attachment point or coupler 124 and proximal end 111 of stabilization tube 110 is fixed within handle 151 at a second attachment point or coupler 128 that is spaced apart from first attachment point or coupler 124. In an embodiment, first attachment point or coupler 124 between outer shaft component 102 and handle 151 is distal to second attachment point or coupler 128 between stabilization tube 110 and handle 151 since stabilization tube 110 is positioned internal to outer shaft component 102 except at a proximal end thereof. Elongated body 114 and distal end 115 of stabilization tube 110 are not attached or fixed to outer shaft component 102. Stated another way, proximal end 111 of stabilization tube 110 is attached to handle 151 and thus is fixed while elongated body 114 and distal end 115 of stabilization tube 110 extend along or within needle lumen 109 of outer shaft component 102 without being attached thereof and thus are not fixed. Stabilization tube 110 and outer shaft component 102 must be fixed or attached to handle 151 at different or longitudinally spaced-apart locations in order for stabilization tube to minimize or eliminate resistive forces exerted onto needle component 134 by outer shaft component 102.

More particularly, the function of stabilization tube 110 is illustrated in the schematic views of FIGS. 6A and 6B. FIG. 6A is a schematic view of a catheter 600A which does not include a stabilization tube depicted within a curved vasculature path 660, while FIG. 6B is a schematic view of a catheter 600B having a stabilization tube 610 depicted within curved vasculature path 660. Catheters 600A, 600B each include a handle 641A, 641B, respectively, and an outer shaft component 602A, 602B, respectively, and the proximal ends of the outer shaft components are fixed or attached to their respective handles. A lesion or occlusion 662 is depicted at a distal end of curved vasculature path 660. Lesion 662 causes or is a source of resistance when a needle component 664 (represented as a dashed line within catheters 600A, 600B in FIGS. 6A, 6B, respectively, for illustrative purposes only) is advanced there-through.

With reference to FIG. 6A, when needle component 664 is advanced through catheter 600A, an advancement force 666 is exerted onto needle component 664 through features or components (buttons, cantilevers, gears, or the like) of handle 641A. As needle component 664 is advanced through a distal portion of catheter 600A, a resistive force 668 acts against the needle component due to the curvature of the catheter (i.e., similar to curved distal portion 120 of needle housing 116 of apparatus 100). More particularly, needle component 664 is straightened when disposed in the catheter and thus resistive force 668 occurs when needle component 664 is moved or advanced through a curve or bend of the catheter. Further, as needle component 664 is advanced through lesion 662, a resistive force 670 acts against the needle component. Resistive forces 672 represent the resistance felt by needle component 664 advancing through catheter 600A due to friction or interference between outer shaft component 602A and needle component 664. Resistive forces 672 cause shaft elongation and stretching of outer shaft component 602A as needle component 634 is advanced there-through. Thus, the amount of force required to advance needle component 664 (i.e., advancement force 666) must overcome several resistive forces that the needle component feels moving through catheter 600A and through lesion 662 (i.e., resistive forces 668, 670, 672). Stated another way, in order to advance needle component 664 through lesion 662, advancement force 666 must be greater than the sum or total of resistive forces 668, 670, 672.

With reference now to FIG. 6B, the presence of stabilization tube 610 eliminates or minimizes resistive forces 672 (which are thus not shown on FIG. 6B). More particularly, catheter 600B includes stabilization tube 610 which is fixed at a spaced apart of different location 674 than outer shaft component 602B within handle 641B. Since the remaining length and distal end of stabilization tube 610 are not fixed, stabilization tube 610 essentially eliminates or prevents friction between needle component 634 and outer shaft component 602B. Stabilization tube 610 may freely elongate, stretch, or otherwise change while needle component 634 is advanced there-through without causing additional resistive forces since the stabilization tube is only fixed at its proximal end. Stabilization tube 610 is not required to elongate but rather elongation may occur depending on the magnitude of the force versus the dimensions plus the material choice of stabilization tube 610. However, outer shaft component 602B does not elongate or stretch during advancement of needle component 634. Thus, due to the presence of stabilization tube 610, the amount of force required to advance needle component 664 (i.e., advancement force 666) in FIG. 6B is reduced or less than the amount of force required to advance needle component 664 (i.e., advancement force 666) in FIG. 6A. In order to advance needle component 664 through lesion 662 in FIG. 6B, advancement force 666 must only be greater than the sum of resistive forces 668, 670. Advancement force 666 is thus preserved for punching and advancing needle component 664 through the distal portion of catheter 600B and through lesion 662 since shaft elongation or stretching of outer shaft component 602B is prevented or minimized.

Referring back to FIG. 4, needle housing 116 will now be described in more detail. As described above, needle housing 116 includes proximal transition portion 118 with a variable flexibility and curved distal portion 120 that bends from the longitudinal axis $L_A$ of occlusion bypassing apparatus 100. Curved distal portion 120 includes a pre-formed or pre-shaped bend or curve. A heat or thermal treatment of the selected material of needle housing 116 may be used to set the shape of curved distal portion 120. More particularly, as shown in FIG. 4, curved distal portion 120 extends, bends, or otherwise curves in a circular path while the remaining length of needle housing 116 is straight and extends parallel to the longitudinal axis $L_A$ of occlusion bypassing apparatus 100. In an embodiment hereof, curved distal portion 120 extends in a circular path and forms a portion of a circle having a radius R. In an embodiment hereof, radius R is 5 mm. Typically, radius R is in the range from 4 mm to 8 mm. As best shown in the sectional views of FIGS. 8 and 9, distal portion 120 of needle housing 116 terminates at side port 108 of outer shaft component 102. The curved distal portion 120 of needle housing 116 functions as a guide to direct needle component 134 through side port 108 such that needle component 134 exits occlusion bypassing apparatus 100 in a stable configuration at a desired orientation for re-entry into a true lumen.

In order to smooth or bridge the transition between flexible stabilization tube 110 and relatively stiffer or less flexible needle housing 116, needle housing 116 includes proximal transition portion 118. Transition portion 118 has a variable flexibility along its length that decreases in a distal direction as indicated by directional arrow 121 (see FIG. 4). Since the flexibility of transition portion 118 decreases in a distal direction, the transition portion allows for a gradual modulation of the flexibility between the flexible stabilization tube 110 (located proximal to transition portion 118) and relatively less flexible, or rigid, remaining length of needle housing 116 (located distal to transition portion 118). The flexibility of occlusion bypassing apparatus 100 corresponds to the flexibility of stabilization tube 110 and needle housing 116, with occlusion bypassing apparatus 100 being more flexible along stabilization tube 110 and less flexible along needle housing 116. Transition portion 118 similarly will provide occlusion bypassing apparatus 100 with a variable flexibility along its length that decreases in a distal direction.

In order to provide transition portion 118 of needle housing 116 with varying flexibility, transition portion 118 includes a plurality of apertures 142, wherein pairs of apertures align with each other along a respective transverse axis of needle housing 116. Each aperture is a cut-out portion or window that increases the flexibility of transition portion 118 as compared to the remaining length of needle housing 118, i.e., straightening portion 123 of needle housing 116 and curved distal portion 120 which have no apertures or cut-out portions formed therein. As used herein, any respective pair of aligned apertures may be referred to singularly or collectively as a pair or pairs of aligned apertures 142. Although shown with seven pairs of aligned apertures 142, a greater or lesser number of pairs of aligned apertures 142 may be used to provide transition portion 118 with varying flexibility. As further described in U.S. patent application Ser. No. 14/460,068 to Guala et al, filed Aug. 14, 2014, which is herein incorporated by reference in its entirety, each aperture in a pair of aligned apertures 142 has an hourglass shape and is disposed from the other aperture of the pair on an opposite side of the perimeter or outer surface of needle housing 116 so as to be diametrically opposed thereto. In order to provide transition portion 118 with varying flexibility along its length that decreases in a distal direction, the pitch or spacing between adjacent pairs of aligned apertures increases in a distal direction. The distance or spacing between adjacent pairs of aligned apertures 142 continues to increase such that distance or spacing between the most distal apertures is the greatest. Since a greater amount of metallic material extends between consecutive pairs of aligned apertures 142, gradually increasing the pitch or spacing between axially adjacent pairs of aligned apertures 142 in the distal direction results in a gradual decrease of flexibility in the distal direction. In addition or in the alternative to varying the spacing between adjacent pairs of aligned apertures 142, in another embodiment the size or area of adjacent pairs of aligned apertures 142 may be varied in order to result in a gradual decrease of flexibility along the length of transition portion 118 in the distal direction as further described in U.S. patent application Ser. No. 14/460,068 to Guala et al, filed Aug. 14, 2014, previously incorporated by reference.

Figure 7:
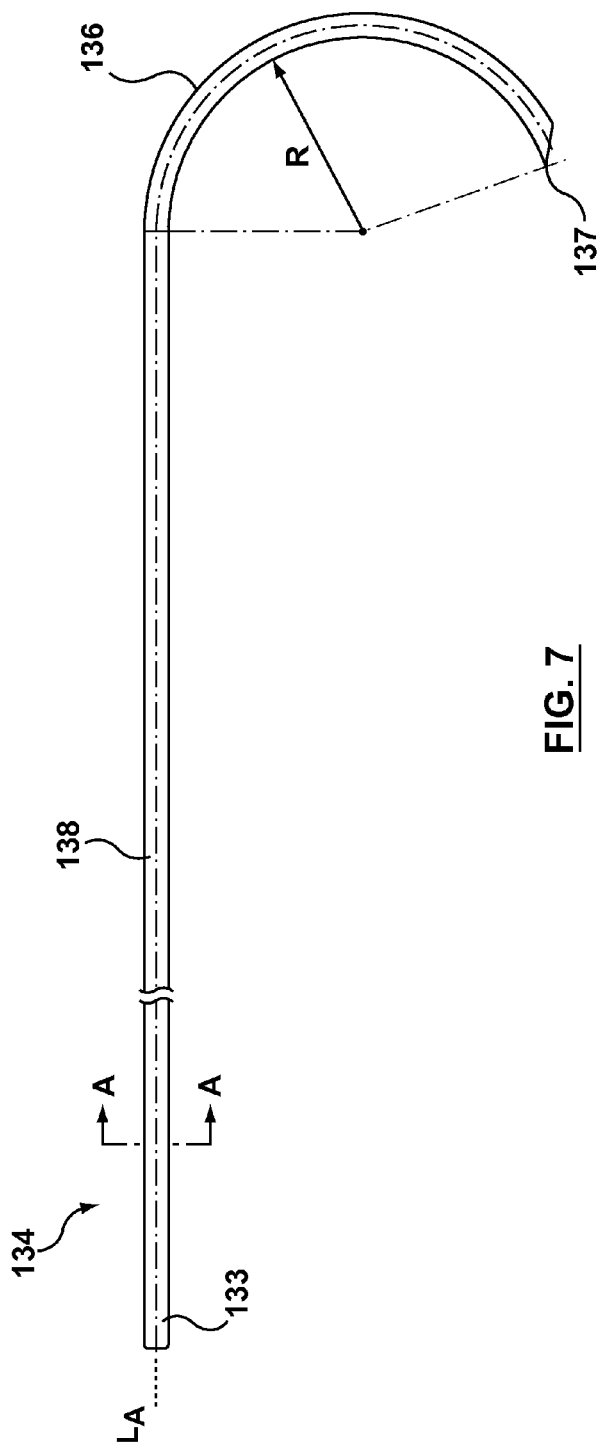
FIG. 7 is a side view of the needle component of the occlusion bypassing apparatus of FIG. 1, wherein the needle component is removed from the occlusion bypassing apparatus.
Figure 7A:
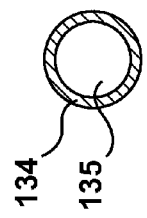
FIG. 7A is a cross-sectional view of the needle component of FIG. 7 taken along line A-A thereof.

Needle component 134, which is shown removed from occlusion bypassing apparatus 100 in FIG. 7, is a tubular or cylindrical element that is configured to be slidably disposed within lumens 112, 127 of stabilization tube 110, needle housing 116, respectively, and removable therefrom. More particularly, needle component 134 is disposed within stabilization tube 110 and needle housing 116 such that there is sufficient space or room there-between for needle component 134 to be movable or slidable in a longitudinal direction relative to stabilization tube 110 and needle housing 116. In order to accommodate a guidewire that may be utilized during a method of subintimally crossing an occlusion as will be discussed in more detail herein, needle component 134 may be a hypotube that defines a lumen 135 therethrough as shown in the cross-sectional view of FIG. 7A. In an embodiment, lumen 135 of needle component 134 is sized to accommodate a guidewire having an outer diameter equal to or less than 0.014 inch such that occlusion bypassing apparatus 100 has a low profile. As shown in FIG. 1, a proximal end 133 of needle component 134 extends out of the patient from hub 152 to be manipulated by a clinician and a distal tip 137 of needle component 134 is configured to pierce or penetrate through a wall of a vessel when extended or deployed.

Needle component 134 includes an elongated first or proximal segment 138 that extends substantially parallel with longitudinal axis $L_A$ of occlusion bypassing apparatus 100 and curved distal end 136 distally extending from a distal end of proximal segment 138. Curved distal end 136 is pre-formed in a bent or curved shape or configuration. More particularly, as shown in FIG. 7, curved distal end 136 extends, bends, or otherwise curves in a circular path. In an embodiment hereof, curved distal end 136 extends in a circular path approximately 160° from a distal end of proximal segment 138, thereby forming a portion of a circle having a radius R. "Approximately" as used herein includes angles with a plus or minus 20° error margin. In an embodiment hereof, radius R is 5 mm. At least curved distal end 136 of needle component 134 is formed from a biocompatible resilient metal such as spring temper stainless steel or nitinol, which utilizes the elastic properties of stress induced martensite, such that a heat or thermal treatment of the selected material may be used to set the shape of curved distal end 136. In an embodiment, needle component 134 may be formed from more than one material, for e.g., with proximal segment 138 being formed of stainless steel and only curved distal end 136 being formed of nitinol. With additional reference to FIG. 4, curved distal portion 120 of needle housing 116 is formed with the same curvature as curved distal end 136 of needle component 134 so that an automatic centering design is obtained. More particularly, curved distal portion 120 of needle housing 116 includes a bend or turn that corresponds with, matches or is the same as the bend or turn of curved distal end 136 of needle component 134. The bend of curved distal portion 120 of needle housing 116 is formed with the same radius R as the bend of curved distal end 136 of needle component 134 so that the needle component 134 exits side port 108 of outer shaft component 102 at or with the correct orientation for re-entry of a true lumen of a vessel. By forming curved distal portion 120 of needle housing 116 and curved distal end 136 of needle component 134 with identical curvatures or radiuses, needle component 134 is very stable inside needle housing 116, thus minimizing any rotation or relative movement between the two components, especially during the needle deployment.

Figure 8:
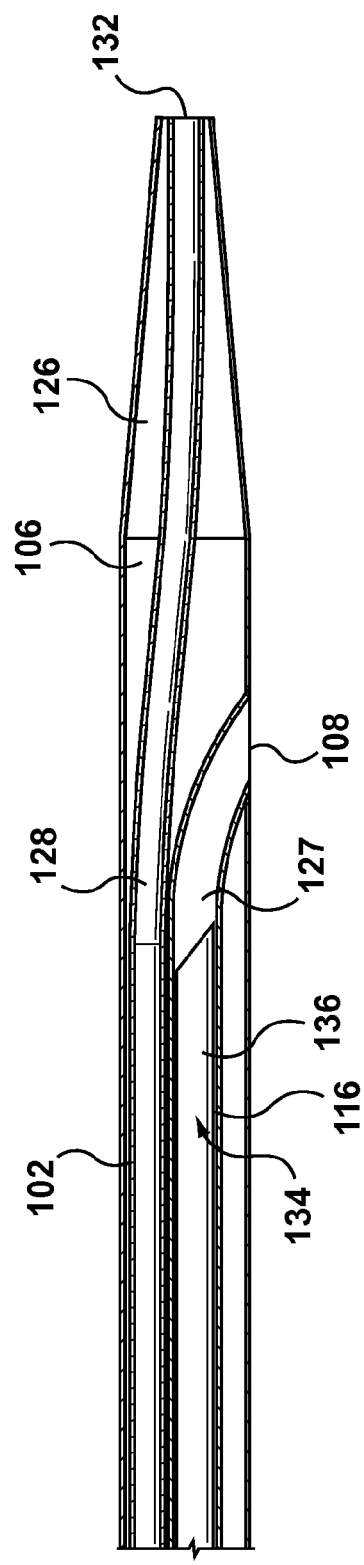
FIG. 8 is a partial longitudinal sectional view of the occlusion bypassing apparatus of FIG. 1 taken along line D-D thereof, wherein a needle component thereof resides within the needle housing of the occlusion bypassing apparatus.

With reference now to FIG. 8, in a first or delivery configuration of the apparatus the curved distal end 136 of needle component 134 is held or restrained in a straightened form within needle housing 116. Balloons 122A, 122B and inflation lumen 125 are not shown in FIG. 8 since the sectional view is taken approximately through the midline of occlusion bypassing apparatus 100. Needle housing 116 is formed from a relatively stiff or less flexible material as described above in order to effectively straighten curved distal end 136 of needle component 134. More particularly, in an embodiment hereof, needle component 134 is pre-loaded within occlusion bypassing apparatus 100 and curved distal end 136 of needle component 134 is held or restrained in a straightened form within straightening portion 123 of needle housing 116 which has no apertures or cut-out portions formed therein. Since transition portion 118 is formed with pairs of aligned apertures 142 to achieve varying flexibility, straightening portion 123 of needle housing 116 with no apertures or cut-out portions is relatively stiffer or less flexible to ensure straightening of curved distal end 136 of needle component 134. Straightening portion 123 of needle housing 116 holds the curved distal end of the needle component in a straightened form during advancement of occlusion bypassing apparatus 100 in the human vasculature.

Figure 9:
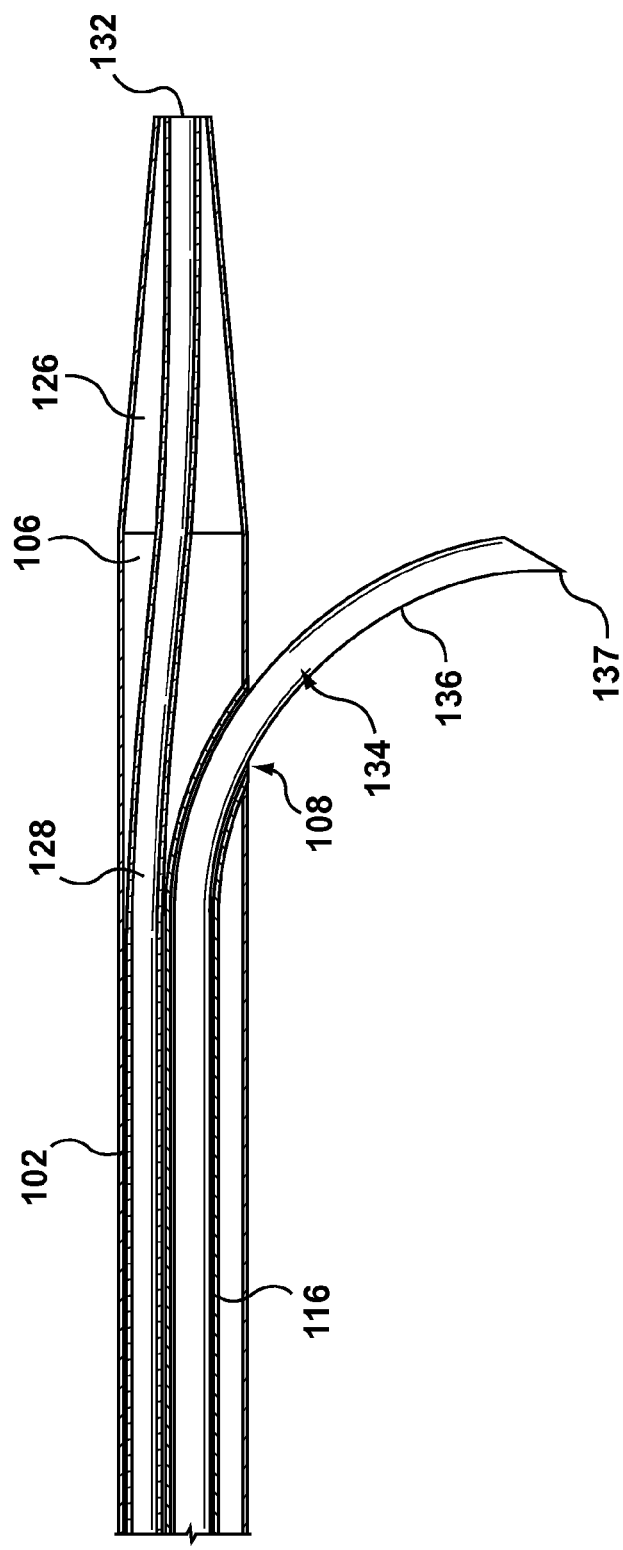
FIG. 9 is a partial longitudinal sectional view of the occlusion bypassing apparatus of FIG. 1 taken along line D-D thereof, wherein a needle component thereof is extended through a side port of an outer shaft component.

In the sectional view of FIG. 9, curved distal end 136 of needle component 134 extends from side port 108 of outer shaft component 102 and bends or curves from longitudinal axis $L_A$ of the apparatus. Balloons 122A, 122B and inflation lumen 125 are not shown in FIG. 9 since the sectional view is taken approximately through the midline of occlusion bypassing apparatus 100. More particularly, when it is desired to distally advance needle component 134 through side port 108 of outer shaft component 102, it must first be confirmed that side port 108 is positioned beyond or distal to the target occlusion and is oriented in the direction of the true lumen of the vessel. The position and orientation of occlusion bypassing apparatus may be monitored via radiopaque markers (not shown) of apparatus 100. Once side port 108 is positioned and oriented as desired, needle component 134 is distally advanced relative to outer shaft component 102 such that curved distal end 136 is no longer constrained by needle housing 116 but rather is extended to protrude from side port 108 of outer shaft component 102. When released from needle housing 116, curved distal end 136 resumes its pre-formed shape or geometry by its own internal restoring forces. As described with respect to FIG. 7, curved distal end 136 extends, bends, or otherwise curves in a circular path, thereby forming a portion of a circle having a radius R. When needle component 134 is distally advanced or extended as best shown in FIGS. 1 and 3, distal tip 137 may be used to penetrate through the vessel wall and re-enter a true lumen of a vessel as described herein. As described above, by forming the bend of curved distal end 136 of needle component 134 with the same curvature or radius as the bend of curved distal portion 120 of needle housing 116, deployed needle component 134 is very stable inside needle housing 116, thus minimizing any rotation or relative movement between the two components. Lateral balloons 122A, 122B may be expanded or inflated to anchor outer shaft component 102 within a subintimal tract either before or after the distal advancement of needle component 134. In an alternative method of the present invention, according to the physician's experience during the procedure he may realize that the subintimal space is sufficiently narrow and suitably envelops the occlusion bypassing apparatus that the latter is properly anchored within the subintimal space. Therefore, in this case there could be no need for expanding the lateral balloons.

Figure 10:
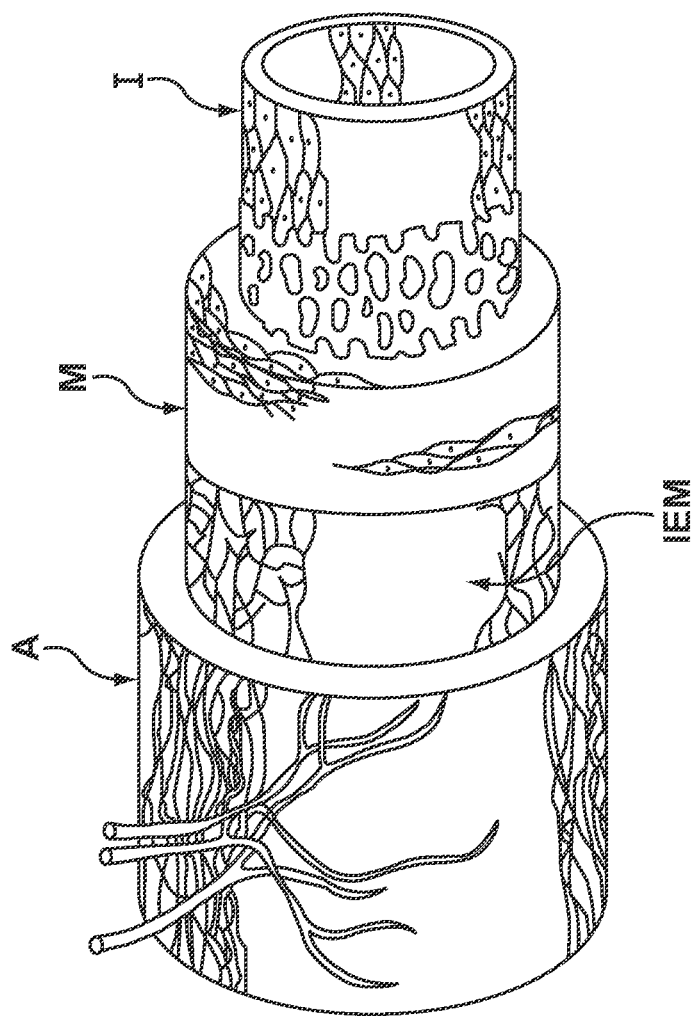
FIG. 10 is a diagram of an artery showing the three layers of tissue that comprise the artery wall.

FIG. 10 is a sectional view of the anatomy of an artery wall, which for purposes of this description is shown to consist essentially of three layers, the tunica intima I ("intima"), tunica media M ("media") which is the thickest layer of the wall, and the tunica adventitia A ("adventitia"). In some arteries an internal elastic membrane IEM is disposed between the media M and adventitia A. The adventitia A is made of collagen, vasa vasorum and nerve cells, the media M is made of smooth muscle cells, and the intima I is made up of a single layer of endothelial cells that provide a nonthrombogenic surface for flowing blood. Occlusion bypassing apparatus 100 is used as part of a system for creating a subintimal reentry tract within a wall of a blood vessel V to allow blood flow around an occlusion. FIGS. 11-18 illustrate an exemplary method of using the above-described occlusion bypassing apparatus 100 to bypass a chronic total occlusion (CTO) according to an embodiment hereof. Although described in relation to bypassing a CTO, it should be understood that the methods and apparatus described herein may be used for bypassing any tight stenoses in arteries or other anatomical conduits and are not limited to total occlusions.

Prior to use of occlusion bypassing apparatus 100 within the vasculature, it may be desirable to flush the apparatus in accordance with techniques known in the field of interventional cardiology and/or interventional radiology. Flushing of occlusion bypassing apparatus 100 may be performed through lumen 135 of needle component 134. More particularly, small openings or holes (not shown) may be provided on needle component 134. In order to perform the initial flushing of occlusion bypassing apparatus 100, side port 108 of outer shaft component 102 is occluded. Saline solution is introduced into a proximal end of lumen 135 of needle component 134 and flushes lumen 135. Since side port 108 is occluded, the saline solution exits from the small holes formed on needle component 134 and flushes lumen 112 of stabilization tube 110 and lumen 127 of needle housing 116.

Figure 11:
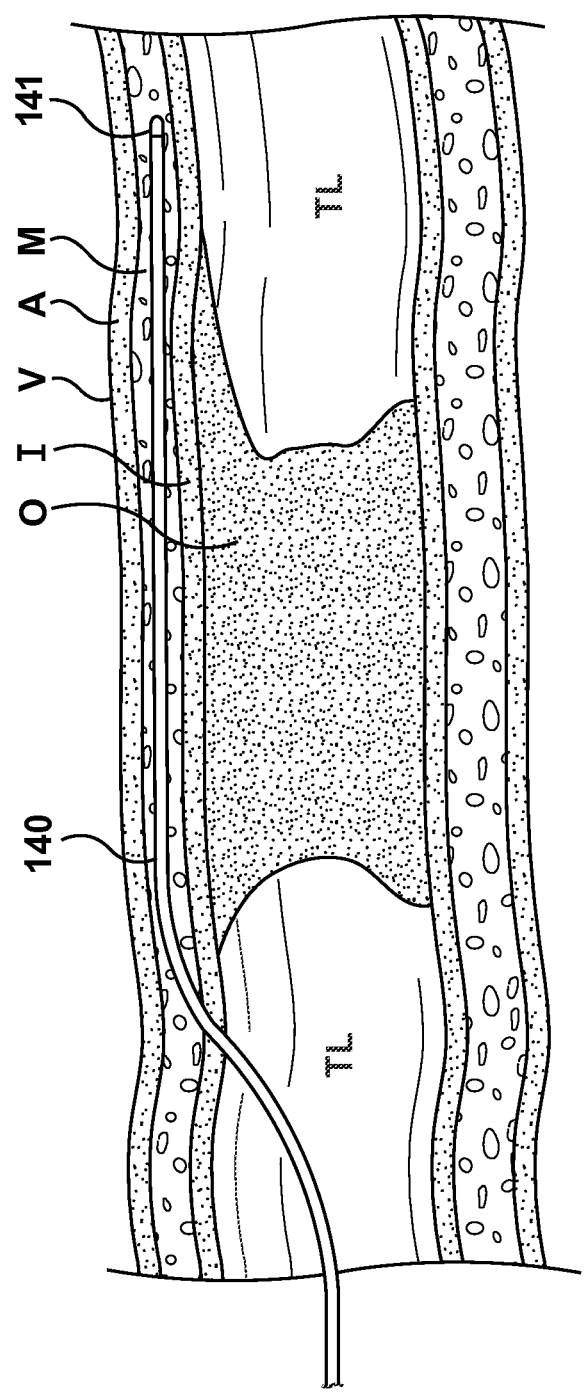
FIG. 11 illustrates a step of a method of crossing an occlusion within a vessel, wherein a guidewire has been transluminally advanced through the vasculature to a position upstream of a treatment site, which in this instance is shown as occlusion O within a true lumen TL of blood vessel V.

As shown in FIG. 11, in accordance with techniques known in the field of interventional cardiology and/or interventional radiology, guidewire 140 having a distal end 141 is transluminally advanced through the vasculature to a position upstream of a treatment site, which in this instance is shown as occlusion O within a true lumen TL of blood vessel V. Guidewire 140 pierces the intima I and is advanced distally to create a subintimal tract by locally dissecting or delaminating intima I from media M or by burrowing through media M. In order to pierce the intima I, a clinician may manipulate distal end 141 of guidewire 140 by prolapsing or bending-over the distal end of guidewire 140 (not shown) and thereafter may use the stiffer arc or loop of the prolapsed distal end to pierce into the intima I to advance guidewire 140 there through. The piercing of the intima I is aided by the fact that typically blood vessel V is diseased, which in some instances makes the intima I prone to piercing. Guidewire 140 is distally advanced within the subintimal tract from a near side of occlusion O to a position where distal end 141 thereof is positioned in the subintimal tract on a far side of occlusion O.

Alternatively, another device other than guidewire 140 initially may be used to create the subintimal tract. Those of ordinary skill in the art will appreciate and understand the types of alternative devices that may be used in this step including an apparatus known as an "olive", a laser wire, an elongate radiofrequency electrode, a microcatheter, or any other device suitable for boring or advancing through the vessel tissue. As another example, a guidewire other than guidewire 140 may be utilized to create the subintimal tract. More particularly, a guidewire having a relatively larger outer diameter than guidewire 140, such as between 0.032-0.040 inches, may be utilized to create the subintimal tract because a larger guidewire has greater column strength to gain access to the subintimal space of vessel V. If an alternative device is used instead of guidewire 140 to form the subintimal tract, such alternative device may be removed and replaced with guidewire 140 after the subintimal tract has been formed.

Figure 12:
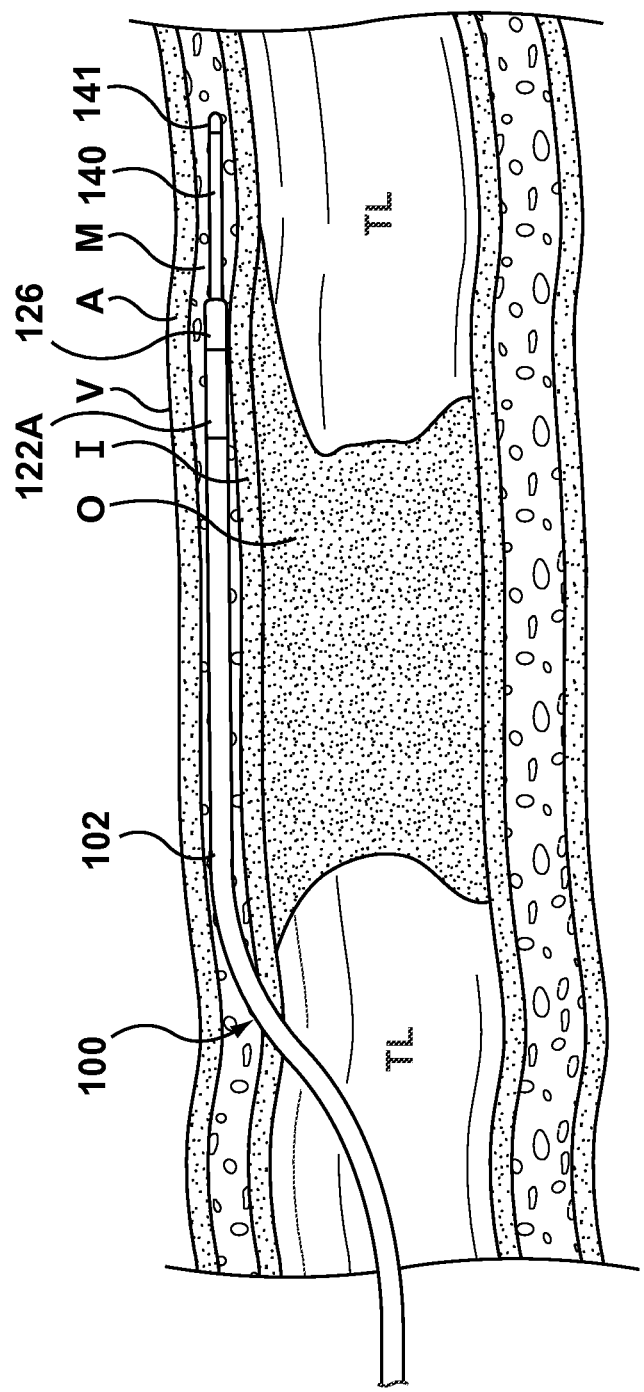
FIG. 12 illustrates another step of a method of crossing an occlusion within a vessel, wherein the occlusion bypassing apparatus of FIG. 1 is tracked over the guidewire.

After the subintimal tract is formed and guidewire 140 is in place as desired, occlusion bypassing apparatus 100 may be tracked over guidewire 140 and advanced such that distal tip 126 is adjacent to the far or downstream end of occlusion O as shown in FIG. 12. In an embodiment, needle component 134 is pre-loaded within occlusion bypassing apparatus 100. During the step of advancing occlusion bypassing apparatus 100 over guidewire 140, curved distal end 136 of needle component 134 is held or restrained in a straightened form within needle housing 116 as described above. In another embodiment, needle component 134 is not positioned or disposed within occlusion bypassing apparatus 100 when occlusion bypassing apparatus 100 is initially advanced over guidewire 140 but rather is subsequently introduced into the apparatus. Utilizing radiopaque markers (not shown) of apparatus 100, occlusion bypassing apparatus 100 should be positioned and oriented such that side port 108 of outer shaft component 102 is positioned beyond or distal to the target occlusion and is oriented in the direction of the true lumen of the vessel.

Figure 13:
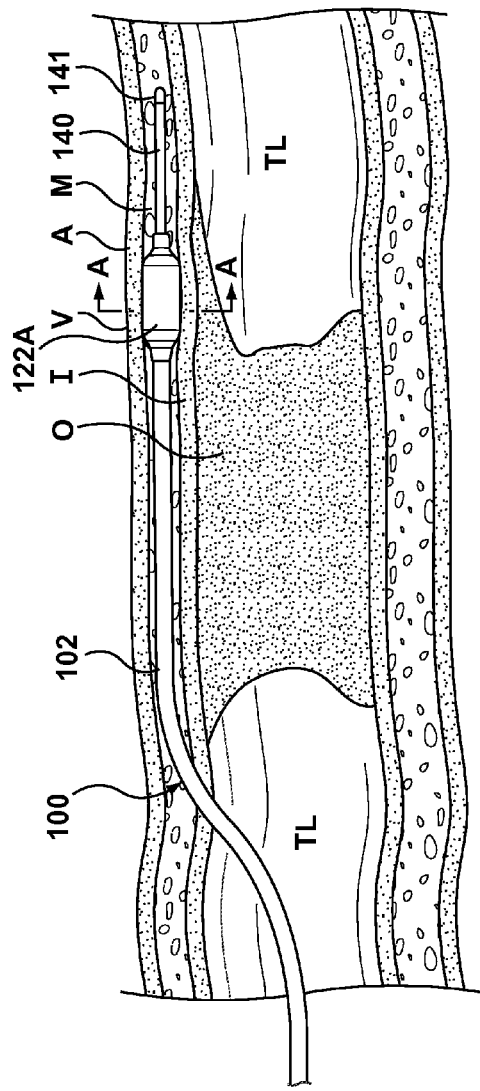
FIG. 13 illustrates another step of a method of crossing an occlusion within a vessel, wherein balloons of the occlusion bypassing apparatus are inflated to anchor the apparatus within the subintimal space.
Figure 13A:
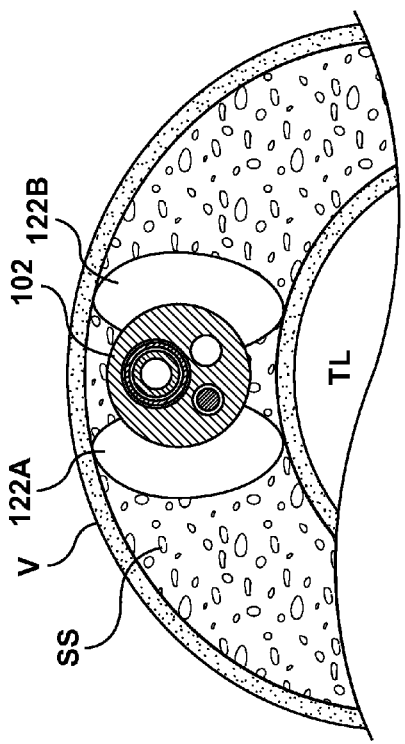
FIG. 13A is a cross-sectional view of a portion of the vessel of FIG. 13, taken along line A-A of FIG. 13.

Once outer shaft component 102 is positioned as desired, lateral balloons 122A, 122B may be expanded or inflated as shown in FIG. 13 and FIG. 13A, thus anchoring outer shaft component 102 in the subintimal tract. FIG. 13A illustrates a cross-sectional view of apparatus 100 within a vessel V having a true lumen TL and a subintimal space SS. The subintimal space SS may be described as having an arc, curve, or C shape. When inflated, lateral balloons 122A, 122B expand into contact with the surrounding patient's anatomy to fill out or occupy the subintimal space SS to improve anchoring and to minimize damage to the surrounding anatomy. In addition, although lateral balloons 122A, 122B are described herein for providing stabilization during distal advancement or deployment of needle component 134, in another embodiment hereof (not shown) inflation of lateral balloons 122A, 122B may also be used to create or assist in creating the subintimal tract. In such an embodiment, lateral balloons 122A, 122B may be inflated multiple times in the subintima to initially support delivery of the occlusion bypassing apparatus across the lesion within the subintima and then subsequently during a re-entry procedure.

Figure 14:
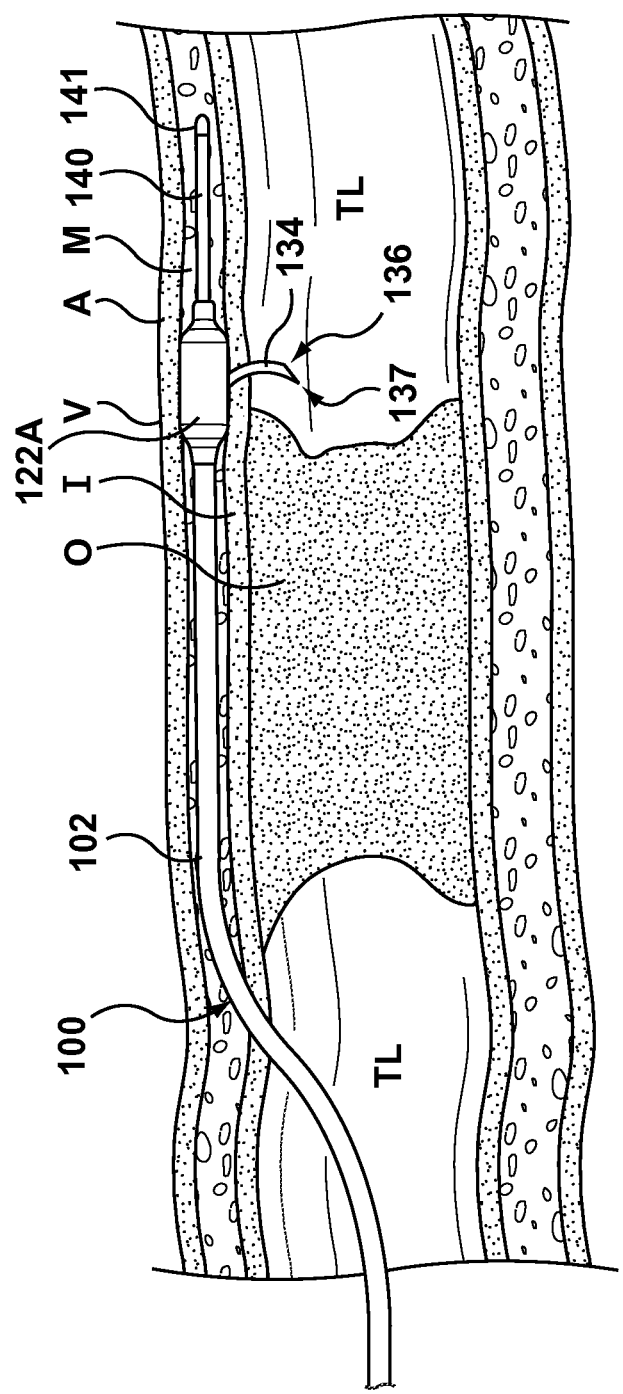
FIG. 14 illustrates another step of a method of crossing an occlusion within a vessel, wherein a needle component of the occlusion bypassing apparatus is distally advanced and deployed out of a side port of the outer shaft component.

With reference to FIG. 14, needle component 134 is then deployed through side port 108 of occlusion bypassing apparatus 100. As explained herein, stabilization tube 110 minimizes or eliminates resistive forces exerted onto needle component 134 by outer shaft component 102 as the needle component is distally advanced through the occlusion bypassing apparatus. Needle component 134 is distally advanced relative to stabilization tube 110 and needle housing 116 until curved distal end 136 extends from or protrudes out of side port 108 of outer shaft component 102 such that distal tip 137 of the needle component penetrates the intima to gain access to the true lumen of the vessel distal to, i.e., downstream of, the CTO. More particularly, needle component 134 is distally advanced relative to outer shaft component 102 (as well as stabilization tube 110 and needle housing 116 housed within outer shaft component 102) such that curved distal end 136 is no longer constrained by needle housing 116 but rather is extended to protrude from side port 108 of outer shaft component 102. When released from needle housing 116, curved distal end 136 resumes its pre-formed shape or geometry by its own internal restoring forces. As described with respect to FIG. 7, curved distal end 136 extends, bends, or otherwise curves in a circular path, thereby forming a portion of a circle having a radius R. When needle component 134 is distally advanced or extended as in FIG. 14, distal tip 137 may be used to penetrate through the vessel wall and re-enter a true lumen of a vessel. As described above, by forming the bend of curved distal end 136 of needle component 134 with the same curvature or radius as the bend of curved distal portion 120 of needle housing 116, deployed needle component 134 is very stable inside needle housing 116, thus minimizing any rotation or relative movement between the two components.

Figure 15:
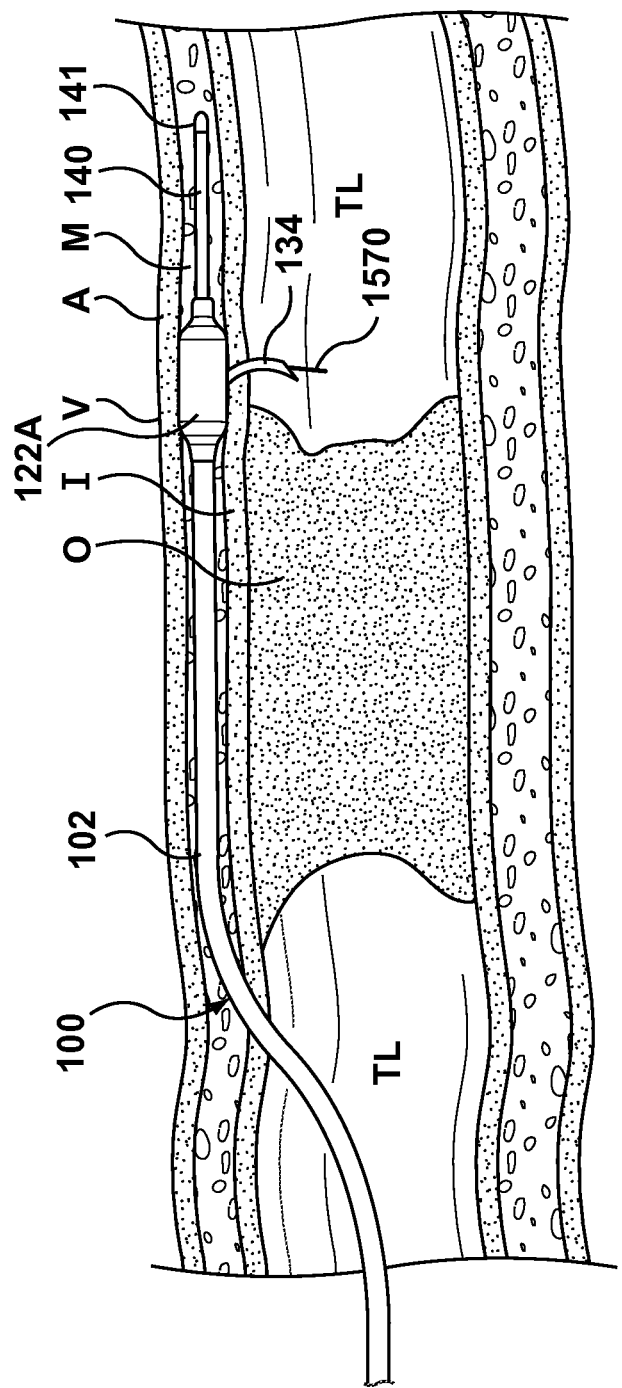
FIG. 15 illustrates another step of a method of crossing an occlusion within a vessel, wherein a second guidewire is advanced through the deployed needle component.
Figure 16:
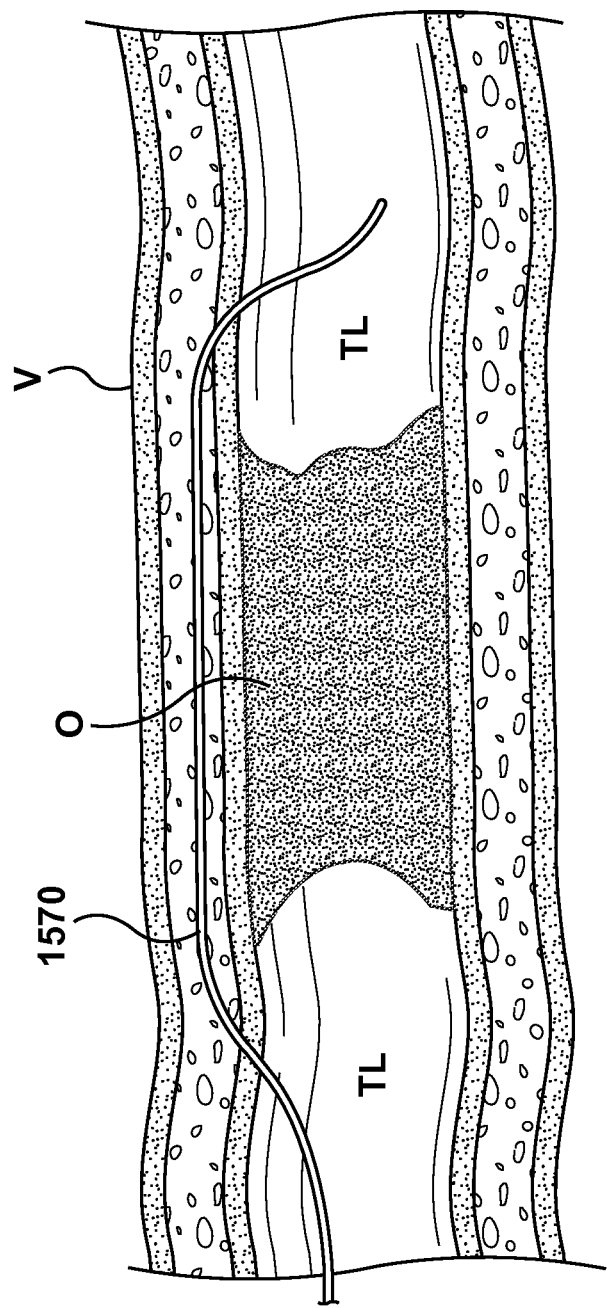
FIG. 16 illustrates another step of a method of crossing an occlusion within a vessel, wherein the occlusion bypassing apparatus is retracted and removed, leaving only the second guidewire in place.

A second guidewire 1570 may be advanced through lumen 135 of needle component 134 and into the true lumen TL of vessel V as shown in FIG. 15. Guidewire 1570 has a relatively smaller outer diameter such as 0.014 inches in order to minimize the size of needle component 134 and subsequently, minimize the size of occlusion bypassing apparatus 100. Additionally, occlusion bypassing apparatus 100 may be removed and guidewire 1570 may be left in place as shown in FIG. 16, with guidewire 1570 extending in true lumen TL proximal to the CTO, through the subintimal tract, and back into true lumen TL distal to the CTO such that the CTO may now be successfully crossed via the pathway or conduit thus created.

Figure 17:
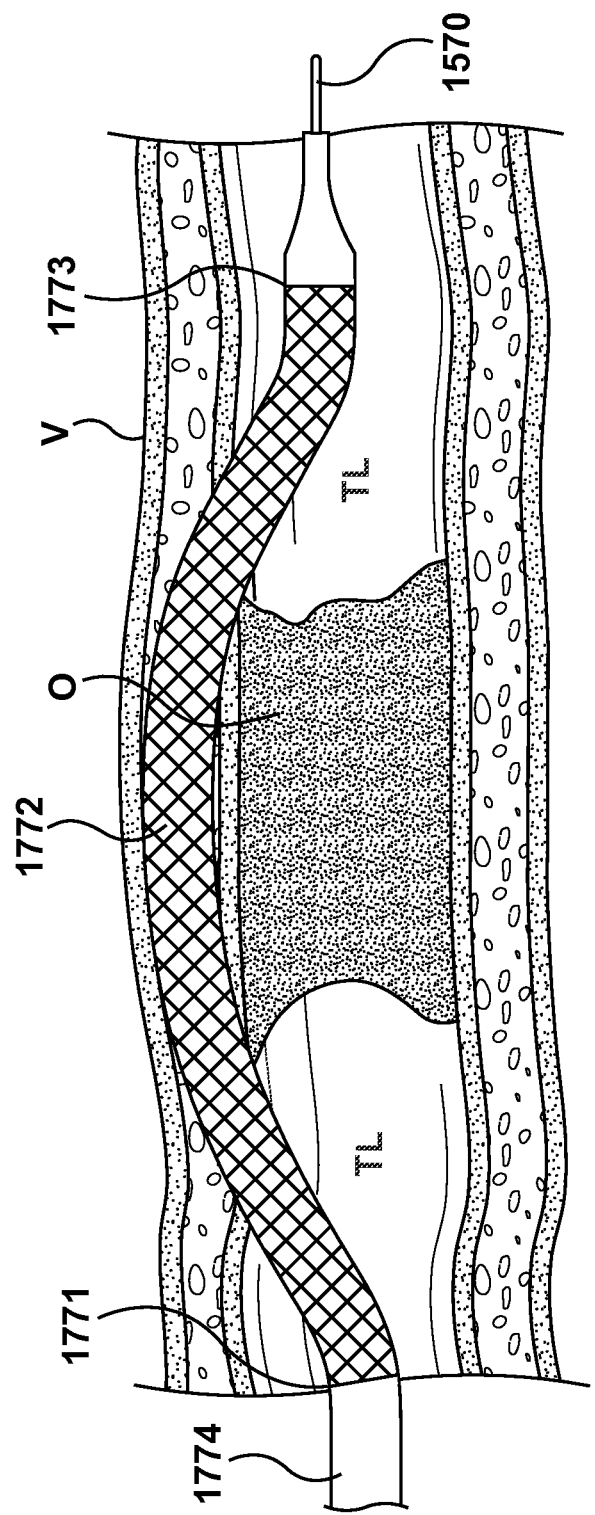
FIG. 17 illustrates another step of a method of crossing an occlusion within a vessel, wherein a stent delivery catheter is tracked over the second guidewire and the stent is expanded.
Figure 18:
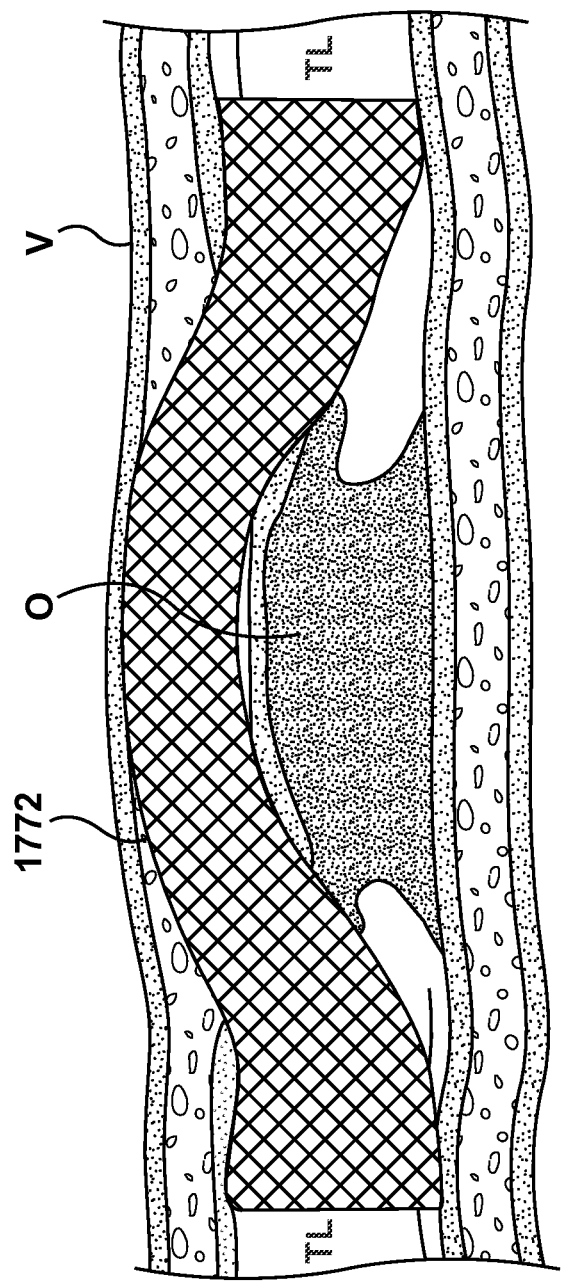
FIG. 18 illustrates another step of a method of crossing an occlusion within a vessel, wherein the stent delivery catheter and second guidewire are retracted and removed, leaving only the expanded stent in place.

Additionally, a covered or uncovered stent may be delivered over guidewire 1570 and implanted within the subintimal tract to facilitate flow from the lumen of the vessel upstream of the CTO, through the subintimal tract and back into the lumen of the vessel downstream of the CTO. FIG. 17 shows a distal end of a catheter 1774 having a stent 1772 mounted thereon being advanced over guidewire 1570 to a position where a distal end 1773 of the radially collapsed stent 1772 is in true lumen TL of vessel V downstream of chronic total occlusion CTO, a proximal end 1771 of stent 1772 is in true lumen TL of vessel V upstream of chronic total occlusion CTO, and a tubular body of stent 1772 extends through the subintimal tract. Stent 1772 is then deployed by either self-expansion or balloon inflation within the subintimal reentry tract to dilate the subintimal tract and compress the adjacent chronic total occlusion CTO. Stent 1772 provides a scaffold which maintains the subintimal tract in an open condition capable of carrying blood downstream of chronic total occlusion CTO. Thereafter, guidewire 1570 and catheter 1774 may be removed from the patient, leaving stent 1772 in an expanded configuration and creating a radially supported, subintimal blood flow channel around chronic total occlusion CTO as seen in FIG. 18. In some cases, it may be desirable to enlarge the diameter of the subintimal tract before advancing stent catheter 1774 into and through it. Such enlargement of the subintimal tract may be accomplished by passing a balloon catheter over guidewire 1570 and inflating the balloon to dilate the tract, or may be any other suitable tract enlarging, dilating or de-bulking instrument that may be passed over guidewire 1570.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An apparatus for bypassing an occlusion in a blood vessel comprising:
   a handle;
   an outer shaft component having a side port proximal to a distal end thereof, the outer shaft component including a needle lumen there-through that includes a curved distal portion that bends from a longitudinal axis of the apparatus and terminates at the side port of the outer shaft component, wherein a proximal end of the outer shaft component is fixed within the handle at a first attachment point;
   a stabilization tube having an elongated body extending between a proximal end and a distal end thereof, the elongated body being disposed within the needle lumen of the outer shaft component, wherein the proximal end of the stabilization tube is fixed within the handle at a second attachment point that is spaced apart from the first attachment point and the elongated body and the distal end of the stabilization tube are not attached to the outer shaft component; and
   a needle component configured to be slidably disposed within the stabilization tube and removable therefrom, wherein the stabilization tube minimizes resistive forces exerted onto the needle component by the outer shaft component.

2. The apparatus of claim 1, wherein the distal end of the stabilization tube is proximal to a proximal end of a needle housing disposed within the needle lumen of the outer shaft component.

3. The apparatus of claim 2, wherein the needle housing is formed from a tube of a shape memory material.

4. The apparatus of claim 2, wherein the needle housing includes a curved distal portion that defines the curved distal portion of the needle lumen and a transition proximal portion that has a variable flexibility along a length thereof that decreases in a distal direction.

5. The apparatus of claim 4, wherein the needle component has a curved distal end with the same curvature as the curved distal portion of the needle housing and a distal tip of the needle component is configured to penetrate a wall of the vessel.

6. The apparatus of claim 5, wherein in a first configuration of the apparatus the curved distal end of the needle component is held in a straightened form within the needle housing and wherein in a second configuration of the apparatus the curved distal end of the needle component extends from the side port of the outer shaft component and bends from the longitudinal axis of the apparatus.

7. The apparatus of claim 1, wherein the outer shaft component includes at least one balloon disposed proximal to the distal end thereof and an inflation lumen in fluid communication with the at least one balloon.

8. The apparatus of claim 1, wherein the outer shaft component also includes a guidewire lumen that extends along at least a portion of the outer shaft component and terminates at a distal port at the distal end of the outer shaft component, the guidewire lumen of the outer shaft component being configured to slidingly receive a guidewire there-through.

9. The apparatus of claim 1, wherein the stabilization tube is formed from a polymeric material.

10. An apparatus for bypassing an occlusion in a blood vessel comprising:
    a handle;
    an outer shaft component having a side port proximal to a distal end thereof and a distal port at the distal end thereof, the outer shaft component including a needle lumen there-through that includes a curved distal portion that bends from a longitudinal axis of the apparatus and terminates at the side port of the outer shaft component, an inflation lumen there-through for receiving an inflation fluid, and a guidewire lumen that extends along at least a portion of the outer shaft component and terminates at the distal port at the distal end of the outer shaft component, wherein a proximal end of the outer shaft component is fixed within the handle at a first attachment point;
    at least one balloon disposed on the outer shaft component proximal to the distal end thereof, wherein the balloon is in fluid communication with the inflation lumen of the outer shaft component;
    a stabilization tube having an elongated body extending between a proximal end and a distal end thereof, the elongated body being disposed within the needle lumen of the outer shaft component, wherein the proximal end of the stabilization tube is fixed within the handle at a second attachment point that is spaced apart from the first attachment point and the elongated body and the distal end of the stabilization tube are not attached to the outer shaft component; and
    a needle component configured to be slidably disposed within the stabilization tube and removable therefrom, wherein the stabilization tube minimizes resistive forces exerted onto the needle component by the outer shaft component.

11. The apparatus of claim 10, wherein the distal end of the stabilization tube is proximal to a proximal end of a needle housing disposed within the needle lumen of the outer shaft component.

12. The apparatus of claim 11, wherein the needle housing is formed from a tube of a shape memory material and the stabilization tube is a polymeric material.

13. The apparatus of claim 11, wherein the needle housing includes a curved distal portion that defines the curved distal portion of the needle lumen and a transition proximal portion that has a variable flexibility along a length thereof that decreases in a distal direction.

14. The apparatus of claim 13, wherein the needle component has a curved distal end with the same curvature as the curved distal portion of the needle housing and a distal tip of the needle component is configured to penetrate a wall of the vessel.

15. The apparatus of claim 14, wherein in a first configuration of the apparatus the curved distal end of the needle component is held in a straightened form within the needle housing and wherein in a second configuration of the apparatus the curved distal end of the needle component extends from the side port of the outer shaft component and bends from the longitudinal axis of the apparatus.

16. An apparatus for bypassing an occlusion in a blood vessel comprising:
- a handle;
- an outer shaft component having a side port proximal to a distal end thereof, the outer shaft component including a needle lumen there-through that includes a curved distal portion that bends from a longitudinal axis of the apparatus and terminates at the side port of the outer shaft component, wherein a proximal end of the outer shaft component is fixed within the handle at a first attachment point;
- a stabilization tube having an elongated body extending between a proximal end and a distal end thereof, the elongated body being disposed within the needle lumen of the outer shaft component, wherein the proximal end of the stabilization tube is fixed within the handle at a second attachment point that is spaced apart from the first attachment point and the elongated body and the distal end of the stabilization tube are not attached to the outer shaft component;
- a needle housing disposed within the needle lumen of the outer shaft component, the needle housing including a curved distal portion that defines the curved distal portion of the needle lumen and a transition proximal portion that has a variable flexibility along a length thereof that decreases in a distal direction, wherein the distal end of the stabilization tube is proximal to a proximal end of the needle housing; and
- a needle component configured to be slidably disposed within the stabilization tube and removable therefrom, the needle component having a curved distal end with the same curvature as the curved distal portion of the needle housing and a distal tip configured to penetrate a wall of the vessel, wherein in a first configuration of the apparatus the curved distal end of the needle component is held in a straightened form within the needle housing and wherein in a second configuration of the apparatus the curved distal end of the needle component extends from the side port of the outer shaft component and bends from the longitudinal axis of the apparatus.

17. The apparatus of claim 16, wherein the needle housing is formed from a tube of a shape memory material.

18. The apparatus of claim 16, wherein the outer shaft component includes at least one balloon disposed proximal to the distal end thereof and an inflation lumen in fluid communication with the at least one balloon.

19. The apparatus of claim 16, wherein the outer shaft component also includes a guidewire lumen that extends along at least a portion of the outer shaft component and terminates at a distal port at the distal end of the outer shaft component, the guidewire lumen of the outer shaft component being configured to slidingly receive a guidewire there-through.

20. The apparatus of claim 16, wherein the stabilization tube is formed from a polymeric material.

* * * * *